US006331525B1

United States Patent
Chiou et al.

(10) Patent No.: US 6,331,525 B1
(45) Date of Patent: *Dec. 18, 2001

(54) TARGETED DELIVERY OF GENES ENCODING INTERFERON

(75) Inventors: Henry C. Chiou, Encinitas; Dennis J. Carlo, Rancho Santa Fe, both of CA (US)

(73) Assignee: The Immune Response Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/379,434

(22) Filed: Aug. 23, 1999

Related U.S. Application Data

(63) Continuation of application No. 08/819,238, filed on Mar. 17, 1997, now Pat. No. 6,069,133, which is a continuation-in-part of application No. 08/616,023, filed on Mar. 14, 1996, now abandoned.

(51) Int. Cl.[7] .............................. A61K 48/00; C12N 15/63

(52) U.S. Cl. ......................... 514/44; 435/320.1; 435/455

(58) Field of Search .................... 424/93.1; 435/69.1, 435/69.5, 320.1, 455; 514/44

(56) References Cited

U.S. PATENT DOCUMENTS 5,166,320 * 11/1992 Wu et al. .............................. 530/395
5,346,696 * 9/1994 Kim et al. ............................ 424/85.4

FOREIGN PATENT DOCUMENTS

| 1 111 159 | 11/1995 | (CN). |
|---|---|---|
| WO 92/19749 | 11/1992 | (WO). |
| WO 92/22310 | 12/1992 | (WO). |
| WO 92/22635 | 12/1992 | (WO). |
| WO 93/07283 | 4/1993 | (WO). |
| WO 93/15609 | 8/1993 | (WO). |
| WO 94/06922 | 3/1994 | (WO). |

OTHER PUBLICATIONS

Baron et al. The interferons: Mechanisms of action and clinical applications. JAMA 266: 1375–1383, Sep. 11, 1991.*
Gewert et al. Analysis of interferon–alfa2 sequences in human genomic DNA. J. of Interferon Res. 13: 227–231, 1993.*
Orkin and Motulsky. Report and recommendations of the panel to assess the NIH investment in research on gene therapy, Dec. 7, 1995.*
Perillo et al. A randomized, controlled trial of interferon alfa–2b alone and after prednisone withdrawal for the treatment of chronic hepatitis B. New Eng. J. of Med. 323: 295–301, Aug. 2, 1990.*
Streuli et al. At least three human type alfa intererons: Structure of alfa2. Science 209: 1343–1347, Sep. 19, 1990.

Abstract from the Second Annula Industry Congress on Hepatitis, entitled "Receptor–Mediated Delivery of Therapeutic Agents for Treatment of Chronic HBV Infections", Bartholomew, R.M. (ciruclated in Jan., 1996).

Baron, S. and F. Dianzani (1994), "The interferons: A biological system with therapeutic potential in viral infections", *Antivir. Res.* 24:97–110.

Coll, et al., "In Vivo Targeting and Specific Transfection of Human Neuroblastoma Cells by chCE7 Antibody–Mediated Gene Transfer", *Gene Therapy*, Abstract provided by the PCT, vol. 4 (2), pp. 156–161 (1997).

"Drug Facts and Comparisons", 1992 Edition, eds., Olin, B.R. et al., St. Louis, MO, pp. 2445–2460.

Hodgson, C. (1995), "Advances in Vector Systems for Gene Therapy," *Exp. Opin. Ther. Patents* 5:459–468.

Miller, N. and Vile, R. (1995), "Targeted Vectors for Gene Therapy," *FASEB J.* 9:190–199.

Mulligan, R. (1993), "The Basic Science of Gene Therapy," *Science* 260, 926–930.

O'Malley, B. and Ledley, F. (1993), "Somatic Gene Therapy," *Arch Otolaryngol Head Neck Surg.* 119:1100–1107.

Slocombe, P. et al. (1982), "High–level Expression of an Interferon α2 Gene Cloned in Phage M13mp7 and Subsequent Purification with a Monoclonal Antibody," *Proc. Natl. Acad. Sci. USA* 79:5455–5459.

Wu, C.H. et al. (1989), "Targeting Genes: Delivery and Persistent Expression of a Foreign Gene Driven by Mammalian Regulatory Elements in Vivo", *J. Biol. Chem.* 264:16985–16987.

Wu, G.Y. and C.H. Wu (1988), "Receptor–mediated Gene Delivery and Expressin in Vivo," *The Journal of Biological Chemistry* 263:14621–14624.

Wu, G.Y. and C.H. Wu (1987), "Receptor–mediated in Vitro Gene Transformation by a Soluble DNA Carrier System", *J. Biol. Chem.* 262:4429–4432.

Wu, G.Y. et al. (1991), "Receptor–mediated Gene Delivery in Vivo," *The Journal of Biological Chemistry* 266:14338–14342.

* cited by examiner

Primary Examiner—Karen M. Hauda
Assistant Examiner—Anne-Marie Baker
(74) Attorney, Agent, or Firm—Lahive & Cockfield, LLP.; Jane E. Remillard, Esq.; Richa K. Nand, Esq.

(57) ABSTRACT

A molecular complex comprising a gene encoding interferon releasably linked to a conjugate of a nucleic acid binding agent and a ligand which binds to a component on the surface of a cell. In a preferred embodiment, the gene encodes human IFN-α, IFN-β, or IFN-γ. The complex can be used to obtain targeted expression of interferon in selected cells either in vivo or in vitro.

14 Claims, 14 Drawing Sheets

```
         1                    11            21            31            41            51
IFN-α2   CDLPQTHSLG    SRRTLMLLAQ    MRRISLFSCL    KDRHDFGFPQ    EEF-GNQFQK    AETIPVLHEM
IFN-α1   CDLPETHSLD    NRRTLMLLAQ    MSRISPSSCL    MDRHDFGFPQ    EEFDGNQFQK    APAISVLHEL 61                   71            81            91           101           111
IFN-α2   IQQIFNLFST    KDSSAAWDET    LLDKFYTELY    QQLNDLEACV    IQGVGVTETP    LMKEDSILAV
IFN-α1   IQQIFNLFTT    KDSSAAWDED    LLDKFCTELY    QQLNDLEACV    MQEERVGETP    LMNADSILAV
                             →
         121                 131           141           151           161
IFN-α2   RKYFQRITLY    LKEKKYSPCA    WEVVRAEIMR    SFSLSTNLQE    SLRSKE
IFN-α1   KKYFRRITLY    LTEKKYSPCA    WEVVRAEIMR    SLSLSTNLQE    RLRRKE
              →
```

Fig. 11A

| | 121 | 125 | 132 | 152 | 161 | 164 | Relative Activity | Relative Enhancement Factor |
|---|---|---|---|---|---|---|---|---|
| IFN-α2 | --- | --- | --- | --- | --- | --- | 1 | 1 |
| IFN-α2-T132 | --- | --- | THR | phe | ser | ser | 0.1 | 0.05 |
| IFN-α2-R125 | --- | ARG | --- | phe | ser | ser | 140 | 200 |
| IFN-α2-K121 | LYS | gln | --- | phe | ser | ser | 17 | 15 |
| IFN-α2-K121R125 | LYS | ARG | --- | phe | ser | ser | 400 | 3000 |
| IFN-α2-R125T132 | --- | ARG | THR | phe | ser | ser | 23 | 10 |
| IFN-α2-K121R125T132 | LYS | ARG | THR | phe | ser | ser | 170 | 150 |
| IFN-α2-H125 | --- | HIS | --- | phe | ser | ser | 9 | |
| IFN-α2-L125 | --- | LEU | --- | phe | ser | ser | 5 | |
| IFN-α2-K125T132 | --- | LYS | THR | phe | ser | ser | 4 | |

Fig. 11B

TARGETED DELIVERY OF GENES ENCODING INTERFERON

RELATED APPLICATIONS

This application is a continuation application of Ser. No. 08/819,238 filed on Mar. 17, 1997, now U.S. Pat. No. 6,069,133, which in turn is a continuation-in-part application of Ser. No. 08/616,023 filed on Mar. 14, 1996, abandoned. The contents of all of the aforementioned application(s) are hereby incorporated by reference.

BACKGROUND OF THE INVENTION

Production of interferons (IFNs) is one of the immune system's non-specific defenses against viruses, microbes, tumors and other antigens. Rather than protecting cells directly, IFNs activate surrounding cells by binding to IFN-specific receptors on these cells, thereby activating the production of intracellular effector proteins (Baron et al. (1994) *Antiviral Res.* 24: 97–110). These effector proteins then mediate various immune responses (e.g., antitumor, antiviral, and immunomodulatory).

Interferons consist of three families of protein molecules, $\alpha$, $\beta$, and $\gamma$, which differ in the agents which induce them and in the cell types which produce them. While there is only one human IFN-$\beta$ gene and one human IFN-$\gamma$ gene, there are at least 17 different human IFN-$\alpha$ genes, each of which likely plays a separate role in modulating specific immune functions. Within these 17 genes, there are also subgroups (variants) of genes. For example, for human IFN-$\alpha$2, there are three subgenes, IFN-$\alpha$2a, IFN-$\alpha$2b and IFN-$\alpha$2c. Human IFN-$\alpha$ is induced by foreign cells, virus-infected cells, tumor cells, bacterial cells and viral envelopes in several types of leukocytes (e.g., B lymphocytes and macrophages). The second type of IFN, IFN-$\beta$, is induced by viral and other foreign nucleic acids in many body cells, including fibroblasts, epithelial cells and macrophages. The third type of IFN, IFN-$\gamma$, is induced in T lymphocytes by foreign antigens for which the T cells have specific receptors. The sequences for most of the aforementioned IFN genes as they occur in nature are published and many have been deposited with the American Type Culture Collection (ATCC) (Rockville, Md.). Specifically, the sequences for human IFN-$\alpha$1 and IFN-$\alpha$2 are published in Weber et al. (1987) *EMBO J.* 6:591–598. The sequence for human IFN-$\alpha$2b is published in Streuli et al. (1980) *Science* 209:1343–1347.

IFNs have a broad variety of therapeutic applications (Baron et al. (1991) *JAMA* 266:1375–1383). Recent advances have led the Food and Drug Administration (FDA) to approve the use of IFNs in the clinical treatment of hairy cell leukemia, condyloma, acuminatum, Kaposi's sarcoma in AIDS patients, and type C hepatitis infection. In addition to these FDA-approved clinical applications, IFN-$\alpha$ has been clinically approved in other countries for approximately 10 other conditions including basal cell carcinoma, non-Hodgkin's lymphoma, multiple myeloma, malignant myeloma, laryngeal papillomatosis, myelogenous leukemia, chronic delta hepatitis infection, and chronic hepatitis B infection (Baron et al. (1991), supra. at 1379).

One area in which the use of IFN therapy holds particular promise is in the treatment of chronic viral infections, such as HIV and hepatitis virus infections. It has been shown that clinically persistent hepatitis B (HBV) and hepatitis C (HBC) infections can be inhibited by administration of exogenous IFN (Hoofnagle (1992), *Interferon: Principles and Medical Applications* (Baron et al. (Eds)), pp. 433–462. For example, recent clinical studies performed on patients infected with chronic HBV demonstrated that administration of $5 \times 10^6$ U of IFN-$\alpha$ daily for sixteen weeks resulted in disappearance of HBV viral DNA and hepatitis Be antigens (Baron et al. (1991), supra. at 1379). While the natural role of IFNs during chronic viral infections has not been determined fully, many variables govern its production and action in vivo, such as the site of production, distribution relative to the site of infection, concentration at the site of infection, and susceptibility of the virus to IFN.

IFN therapy currently involves administration of exogenous IFN to patients, generally by IV injection, on a frequent (e.g., daily) basis. High dosages are often required to achieve a sufficient concentration of IFN in target tissues (e.g., tissues surrounding infected cells). In addition, patients often experience a variety of adverse side effects and/or peripheral toxicities associated with systemic delivery of IFN.

Improved forms of IFN replacement therapy would be of great therapeutic value.

SUMMARY OF THE INVENTION

The present invention provides a molecular complex for targeted delivery of genes encoding interferon (IFN) to selected cells. The complex comprises a gene encoding an IFN protein, preferably human IFN-$\alpha$, IFN-$\beta$ or IFN-$\gamma$, releasably linked to a carrier molecule made up of a nucleic acid binding agent (e.g., a polycation) and a ligand which binds to a component on the surface of a target cell and is consequently internalized by the cell. In a preferred embodiment, the gene encodes human IFN-$\alpha$2b having the amino acid sequence shown in FIG. 11 (SEQ ID NO:1).

The molecular complex can be targeted to a variety of cells via the carrier portion of the molecular complex. In one embodiment, the ligand of the carrier binds to the asialoglycoprotein receptor on liver cells. In another embodiment, the ligand is an antibody directed against the CD3 or CD5 receptor on T and B cells.

The molecular complex can be delivered to selected cells in vivo to treat a wide variety of diseases which are responsive to IFN therapy. Alternatively, the molecular complex can be delivered to selected cells in vitro (in culture) to produce recombinant IFN which can be administered as exogenous protein to patients in conventional IFN protein therapy.

BRIEF DESCRIPTION OF THE FIGURES

FIGS. 11A and 11B show the aligned amino acid sequences of mature human IFN-α2 (SEQ ID NO:1) and IFN-α1 (SEQ ID NO:2). The 28 amino acids which differ between the two sequences are underlined. The two arrows show the two amino acid substitutions made in the IFN-α2 protein to increase biological activity (when recombinantly expressed in mice) compared to the unsubstituted IFN-α2 protein, as demonstrated in FIG. 12. These two amino acid substitutions are derived from the IFN-α1 sequence (as shown in the Figure) and correspond to the IFN-2α-K121R125 protein shown in Panel B. Panel B shows the effect of various single amino acid substitutions (SEQ ID NOS:3–12) on antiviral activity (on mouse cells) for human IFN-α2b. The arrow indicates the IFN-α2b hybrid containing the two amino acid substitutions indicated by arrows in Panel A. The "Enhancement Factor" is the factor by which antiviral activity increases upon substituting the amino acids indicated. Amino acids written in lower case are derived from IFN-α2. Amino acids written in upper case represent residues of IFN-α1.

DETAILED DESCRIPTION OF THE INVENTION

Figure 1:
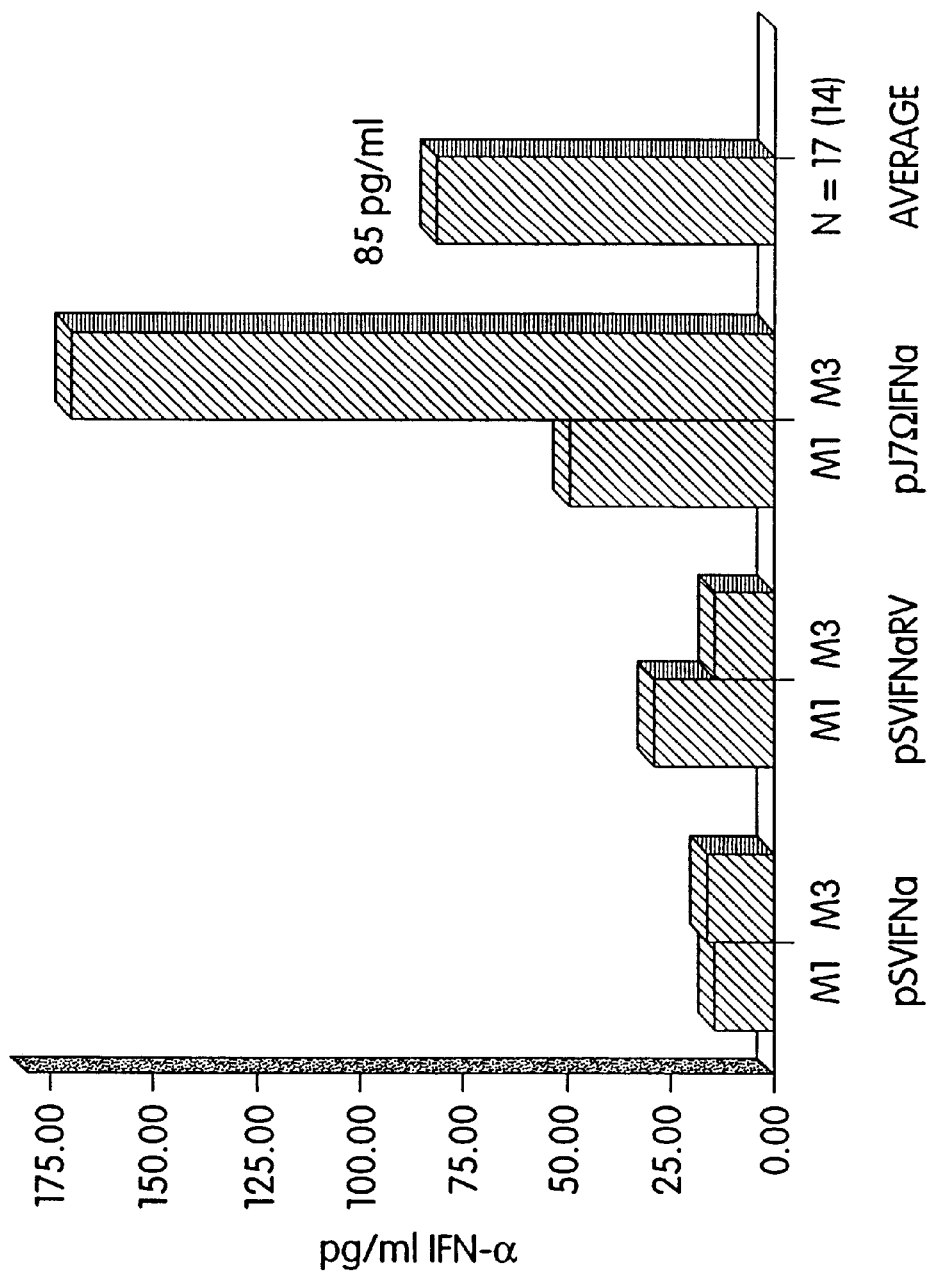
FIG. 1 is a graphic representation of IFN-$\alpha$ expression levels (pg/ml IFN-$\alpha$) in mice injected with various plasmids encoding human IFN-$\alpha$2b. The plasmids were administered in the form of a targeted molecular complex made up of the plasmid complexed to a carrier molecule of polylysine and asialoorosomucoid which binds to the asialoglycoprotein receptor present on liver cells.

The present invention provides a soluble molecular complex comprising a gene encoding interferon (IFN), and to a method of using the complex to selectively deliver the gene to a target cell to obtain expression of the gene either in vivo or in vitro. The IFN gene of the complex is releasably linked to a carrier molecule comprising a gene binding agent and a ligand which binds to a component on the surface of the target cell. Following binding of the ligand of the complex to the cell, the complex is internalized by the cell (e.g., by endocytosis). In all cases, the complex is soluble in solution so that it can pass through physiological barriers when administered in vivo to reach target cells or tissues.

I. The Interferon Gene

The gene of the molecular complex can encode any form of IFN. In a preferred embodiment, the gene encodes a human form of IFN. This includes the three known types of human IFN, IFN-α, IFN-β, and IFN-γ. The gene can also be a chimeric IFN gene, for example, to reduce antigenicity of the encoded protein.

While there is only one known gene encoding human IFN-β and IFN-γ, there are at least seventeen known genes encoding human IFN-α (Baron et al. supra.). The present invention encompasses the targeted delivery of any of these known IFN genes, many of which can be obtained from the American Type Culture Collection (Rockville, Md.). In addition, the nucleotide sequences of many of these genes have been published and are therefore publicly available. For example, the amino acid sequences (from which the corresponding nucleotide sequence can be deduced) of human IFN-α1 (SEQ ID NO:2) and IFN-α2 (SEQ ID NO:1) are published in Weber et al. (1987) *EMBO J.* 6:591–598. In addition, the nucleotide sequence encoding human IFN-α2b is published in Streuli et al. (1980) *Science* 209:1343–1347 and can be obtained as a cDNA clone from the ATCC as plasmid pALCA1SIFN (ATCC deposit #53369).

The gene can be DNA (cDNA or genomic DNA), RNA, or an analogue thereof and comprises a sequence encoding IFN in a form suitable for expression and preferably also processing and secretion of the encoded interferon protein by the target cell. Accordingly, the gene contains not only the sequence encoding IFN, but is also operably linked to genetic regulatory sequences necessary for transcription of the gene (i.e., linked in a manner whereby the regulatory sequences are able to assert their effect (i.e., function) upon transcription of the gene), including for example promoters and enhancers. These transcription regulatory elements can be the natural sequences or, alternatively, they may be exogenous sequences, such as those from other eukaryotic or viral genes. For example, suitable promoters include a broad variety of viral promoters, such as SV40 and CMV promoters. Transcription regulatory elements may also include sequences which lead to constitutive or inducible transcription of the gene. Transcription regulatory sequences are well known in the art and are described in Goeddel, *Gene expression Technology: Methods in Enzymology*, p. 185, Academic Press, San Diego, Calif. (1990).

In order to increase stability and/or translational efficiency of the mRNA transcribed from the gene, the 5' and/or 3' untranslated sequences flanking the sequence encoding the IFN protein can be removed, modified or replaced by sequences from other genes. In one embodiment, the human IFN-α2b gene (Streuli et al. (1980), supra.) is modified by removing a region of the 3' non-coding sequence extending from the EcoRi restriction site to the SPE-1 restriction site.

The sequence encoding the IFN protein also contains the appropriate signal sequences which provide for intracellular trafficking and/or secretion of the protein. The sequence encoding the IFN protein may still further contain specific sequences necessary for appropriate postranslational modification of the protein, such as phosphorylation, glycosylation and farnesylation.

In one embodiment, the sequence encoding the IFN protein is inserted into an expression vector, such as a plasmid, or a transposable genetic element, which contains any or all of the aforementioned genetic regulatory and processing sequences (e.g., promoter and enhancer elements). A preferred expression vector for use in the complex is pJ7Ω (Morgenstern et al. (1990) *Nucl. Acids Res.* 18(4):1068). This vector may contain a suitable promoter to drive transcription of the gene, such as the CMV promoter or the thyroxin binding globulin (TBG) promoter (Hayashi et al. (1993) *Molec. Endocrinol.* 7:1049–1060). The vector may also contain a suitable enhancer such as the CMV enhancer or the alpha-1 microglobulin/bikunin enhancer (Rouet et al. (1992) *J. Biol. Chem.* 267:20765–20773). The vector may also contain suitable introns and/or polyadenylation signals to increase expression and direct intracellular trafficking of the gene transcript, such as the SV40 small t intron (IVS) and SV40 polyadenylation signal. Several plasmid constructs suitable for use in the invention, including those which employ pJ7Ω as a backbone, are shown in FIGS. 3–8. However other plasmids in which known IFN genes can be inserted for expression by cells can be constructed by those of ordinary skill in the art using known materials and techniques. Accordingly, any and all such constructs are included within the scope of the present invention.

II The Carrier Molecule

The IFN gene is releasably linked to a carrier molecule made up of a nucleic acid binding agent and a ligand which binds to a component on the surface of a cell, thereby forming a polynucleotide-carrier complex. The carrier molecule of the polynucleotide-carrier complex performs at least two functions: (1) it binds the gene encoding IFN (e.g., in an expression plasmid) in a manner which is sufficiently stable (either in vivo, ex vivo, or in vitro) to prevent significant uncoupling of the polynucleotide extracellularly prior to internalization by a target cell, and (2) it binds to a component on the surface of a target cell so that the polynucleotide-carrier complex is internalized by the cell. Generally, the carrier is made up of a cell-specific ligand and a cationic moiety which, for example, are conjugated. The cell-specific ligand binds to a cell surface component, such as a protein, polypeptide, carbohydrate, lipid or combination thereof. It typically binds to a cell surface receptor. The cationic moiety binds, e.g., electrostatically, to the polynucleotide.

The ligand of the carrier molecule can be any natural or synthetic ligand which binds a cell surface receptor. The ligand can be a protein, polypeptide, glycoprotein, glycopeptide or glycolipid which has functional groups that are exposed sufficiently to be recognized by the cell surface component. It can also be a component of a biological organism such as a virus, cells (e.g., mammalian, bacterial, protozoan).

Alternatively, the ligand can comprise an antibody, antibody fragment (e.g., an F(ab')$_2$ fragment) or analogues thereof (e.g., single chain antibodies) which binds the cell surface component (see e.g., Chen et al. (1994) *FEBS Letters* 338:167–169, Ferkol et al. (1993) *J. Clin. Invest.* 92:2394–2400, and Rojanasakul et al. (1994) *Pharmaceutical Res.* 11(12):1731–1736). Such antibodies can be produced by standard procedures.

Ligands useful in forming the carrier will vary according to the particular cell to be targeted. For targeting hepatocytes, proteins and polypeptides containing galactose-terminal carbohydrates, such as carbohydrate trees obtained from natural glycoproteins, can be used. For example, natural glycoproteins that either contain terminal galactose residues or can be enzymatically treated to expose terminal galactose residues (e.g., by chemical or enzymatic desialylation) can be used. In one embodiment, the ligand is an asialoglycoprotein, such as asialoorosomucoid, asialofetuin or desialylated vesicular stomatitis virus.

Alternatively, suitable ligands for targeting hepatocytes can be prepared by chemically coupling galactose-terminal carbohydrates (e.g., galactose, mannose, lactose, arabinogalactan etc.) to nongalactose-bearing proteins or polypeptides (e.g., polycations) by, for example, reductive lactosamination. Methods of forming a broad variety of other synthetic glycoproteins having exposed terminal galactose residues, all of which can be used to target hepatocytes, are described, for example, by Chen et al. (1994) *Human Gene Therapy* 5:429–435 and Ferkol et al. (1993) *FASEB* 7: 1081–1091 (galactosylation of polycationic histones and albumins using EDC); Perales et al. (1994) PNAS 91:4086–4090 and Midoux et al. (1993) *Nucleic Acids Research* 21(4):871–878 (lactosylation and galactosylation of polylysine using α-D-galactopyranosyl phenylisothiocyanate and 4-isothiocyanatophenyl β-D-lactoside); Martinez-Fong (1994) *Hepatology* 20(6):1602–1608 (lactosylation of polylysine using sodium cyanoborohydride and preparation of asialofetuin-polylysine conjugates using SPDP); and Plank et al. (1992) *Bioconjugate Chem.* 3:533–539 (reductive coupling of four terminal galactose residues to a synthetic carrier peptide, followed by linking the carrier to polylysine using SPDP).

For targeting the polynucleotide-carrier complex to other cell surface receptors, particularly cells which naturally produce IFN proteins, the carrier component of the complex can comprise other types of ligands. For example, mannose can be used to target Kupffer cells and macrophages, which naturally produce IFN-αs. Mannose 6-phosphate glycoproteins can be used to target fibroblasts, which naturally produce IFN-β. Pulmonary surfactants, such as Protein A, can be used to target epithelial cells, which naturally produce IFN-β (see e.g., Ross et al. (1995) *Human Gene Therapy* 6:31–40). Anti-secretory component antibodies can also be used to target the polymeric immunoglobulin receptor on lung and liver epithelial cells which naturally produce IFN-β (see e.g., Perales et al. (1994) *Eur. J. Biochem.* 226: 255–266). Transferrin can be used to target smooth muscle cells (see e.g., Wagner et al. (1990) *PNAS* 87:3410–3414 and U.S. Pat. No. 5,354,844 (Beug et al.)). Intrinsic factor-vitamin B12 and bile acids (see e.g., Kramer et al. (1992) *J. Biol. Chem.* 267:18598–18604) can be used to target enterocytes. Insulin can be used to target fat cells and muscle cells (see e.g., Rosenkranz et al. (1992) *Experimental Cell Research* 199:323–329 and Huckett et al. (1990) *Chemical Pharmacology* 40(2):253–263). Apolipoprotein E can be used to target nerve cells.

The cationic moiety of the carrier molecule can be any positively charged species capable of electrostatically binding to negatively charged polynucleotides. Preferred cationic moieties for use in the carrier are polycations, such as polylysine (e.g., poly-L-lysine), polyarginine, polyornithine, spermine, basic proteins such as histones (Chen et al., supra.), avidin, protamines (see e.g., Wagner et al., supra.), modified albumin (i.e., N-acylurea albumin) (see e.g., Huckett et al., supra.) and polyamidoamine cascade polymers (see e.g., Haensler et al. (1993) *Bioconjugate Chem.* 4: 372–379). A preferred polycation is polylysine (e.g., ranging from 3,800 to 60,000 daltons).

In one embodiment, the carrier comprises polylysine having a molecular weight of about 17,000 daltons (purchased as the hydrogen bromide salt having a MW of a 26,000 daltons), corresponding to a chain length of approximately 100–120 lysine residues. In another embodiment, the carrier comprises a polycation having a molecular weight of about 2,600 daltons (purchased as the hydrogen bromide salt having a MW of a 4,000 daltons), corresponding to a chain length of approximately 15–10 lysine residues.

The carrier can be formed by linking a cationic moiety and a cell-specific ligand using standard cross-linking reagents which are well known in the art. The linkage is typically covalent. A preferred linkage is a peptide bond. This can be formed with a water soluble carbodiimide, such as 1-ethyl-3-(3-dimethylaminopropyl)carbodiimide hydrochloride (EDC), as described by McKee et al (1994) *Bioconiugate Chem.* 5: 306–311 or Jung, G. et al. (1981) *Biochem. Biophys. Res. Commun.* 101: 599–606 or Grabarek et al. (1990) *Anal. Biochem.* 185:131. Alternative linkages are disulfide bonds which can be formed using cross-linking reagents, such as N-Succinimidyl 3-(2-pyridyldithio) propionate (SPDP), N-hydroxysuccinimidyl ester of chlorarnbucil, N-Succinimidyl-(4-Iodoacetyl) aminobenzoate) (SIAB), Sulfo-SIAB, and Sulfo-succinimidyl-4-maleimidophenyl-butyrate (Sulfo-SMPB). Strong noncovalent linkages, such as avidin-biotin interactions, can also be used to link cationic moieties to a variety of cell binding agents to form suitable carrier molecules.

The linkage reaction can be optimized for the particular cationic moiety and cell binding agent used to form the carrier. The optimal ratio (w:w) of cationic moiety to cell binding agent can be determined empirically. This ratio will vary with the size of the cationic moiety (e.g., polycation) being used in the carrier, and with the size of the polynucleotide to be complexed. However, this ratio generally ranges from about 0.2–5.0 (cationic moiety: ligand). Uncoupled components and aggregates can be separated from the carrier by molecular sieve or ion exchange chromatography (e.g., Aquapore™ cation exchange, Rainin).

In one embodiment of the invention, a carrier made up of a conjugate of asialoorosomucoid and polylysine is formed with the cross linking agent 1-(3-dimethylaminopropyl)-3-ethyl carbodiimide. After dialysis, the conjugate is separated from unconjugated components by preparative acid-urea polyacrylamide gel electrophoresis (pH 4–5). The conjugate can be further purified on the carboxymethyl functionalized column (see U.S. patent application Ser. No. 08/043,008, filed Apr. 5, 1993, now abandoned, the teachings of which are incorporated by reference herein).

When the carrier molecule comprises a cationic component (e.g., a polycation which electrostatically binds the gene), aggregation of carrier molecules can occur, likely due to intermolecular and intramolecular associations (e.g., hydrogen bonding) involving the net positive charge of the carrier molecules. Accordingly, in a preferred embodiment of the invention, the carrier molecule is formed in a solution containing a sufficient amount of a charge shielding agent to inhibit aggregation of the carrier molecules (i.e., aggregation which would occur in the absence of a charge shielding agent). In one embodiment, the carrier solution is prepared by forming carrier molecules, as described above (e.g., by conjugation of a cationic moiety and a cell binding agent), and then mixing the carrier molecules with a sufficient amount of a charge shielding agent to inhibit aggregation of the carrier molecules.

The term "charge shielding agent", as used herein, is intended to include any agent which is capable of (a) reducing charge interactions (e.g., hydrogen bonding) between individual cationic carrier molecules and/or between different parts of the same carrier molecule; and/or (b) reducing charge interactions between cationic carrier molecules and the solvent.

The term "inhibit aggregation," as used herein, refers to disaggregation and/or to prevention of aggregation of cationic carrier molecules.

The term "sufficient to inhibit aggregation of the carrier molecules," as used herein, refers to a level of disaggregation at which the carrier molecules, when complexed to polynucleotide, are easily taken up by cells and/or can easily pass through physiological barriers (e.g., blood/tissue barriers). Generally, this level of dispersity is achieved when the carrier molecules have a radius of about 20 nm or less, preferably about 15 nm or less and most preferably about 10 nm or less, as measured by laser light scattering analysis.

Other methods of determining the level of aggregation of carrier molecules (alone or complexed to polynucleotide) include, for example, sucrose density gradient analysis, electron microscopy (EM), circular dichroism (CD), and spectrophotometry (e.g., absorbance at 260 nm).

In a preferred embodiment of the invention, the charge shielding agent is a salt. Suitable salts include, for example, sodium chloride (NaCl), sodium sulfate ($Na_2SO_4$), sodium phosphate ($NaH_2PO_4$), ammonium sulfate (($NH_4)SO_4$), ammonium phosphate ($NH_4H_2PO_4$), potassium sulfate ($K_2SO_4$), potassium phosphate ($KH_2PO_4$), potassium chloride (KCl), magnesium sulfate ($MgSO_4$), magnesium phosphate ($MgHPO_4$), magnesium chloride ($MgCl_2$), and lithium chloride (LiCl) and a variety of others. In a particularly preferred embodiment, the salt is sodium chloride (NaCl).

Other charge shielding agents which can be used to substantially disaggregate the carrier molecules include, for example, detergents and amphiphile surfactants such as the BRIJ family of polyoxyethylene fatty ethers, the SPAN sorbitan fatty acid esters, and the TWEEN polyoxyethylene derivatives of sorbitan fatty acid esters, all available from ICI Americas, Inc. of Wilmington, Del.

When using a salt (e.g., NaCl) as the charge shielding agent, the appropriate amount of salt to inhibit aggregation of the carrier molecules will vary according to the concentration of the carrier molecules. However, this concentration is generally at least about 1.0 M or more. For example, for solutions containing carrier molecules at a concentration of about 0.5–20 mg/mL, the salt can be added to a concentration of about 1.0–10 M. In a preferred embodiment, the carrier molecules are present in the carrier solution at a concentration of about 3.0–7.0 mg/mL, preferably about 5.0–6.0 mg/mL, and most preferably about 5.6 mg/mL. At these concentrations of carrier molecules, the carrier solutions can be prepared with salt concentrations of about 1.0–5.0 M, preferably about 4.0–5.0 M, and most preferably about 4.7 M, respectively.

However, the appropriate amount of any given charge shielding agent to inhibit aggregation of carrier molecules can be determined empirically. For example, samples of carrier molecules can be prepared at various concentrations of a charge shielding agent as previously described, and the level of aggregation of the carrier molecules can then be examined by any of the techniques disclosed above (e.g., laser light scattering analysis, sucrose density gradient analysis, electron microscopy (EM), circular dichroism (CD), and spectrophotometry).

In addition to a charge shielding agent, the carrier solution can also optionally contain other dispersing agents to further inhibit aggregation of the carrier molecules. As previously described, aggregation of cationic carrier molecules is believed to result largely from intermolecular and intramolecular associations (e.g., hydrogen bonding) involving the net positive charge of the carrier molecules. Agents which reduce the net positive charge of the carrier molecules, therefore, can diminish these molecular associations and promote dispersity of the cationic carrier molecules.

Accordingly, in one embodiment of the invention, the carrier solution comprises a charge neutralizing agent, in addition to the charge shielding agent. The term "charge neutralizing agent", as used herein, is intended to include any agent capable of neutralizing a portion of the positive charge of cationic carrier molecules (i.e., by deprotonation). In a preferred embodiment of the invention, the charge neutralizing agent is a base. Suitable bases include, for example, sodium hydroxide (NaOH), potassium hydroxide (KOH), ammonium hydroxide ($NH_4OH$), alkylamines, alkoxides and triethanolamines. In a particularly preferred embodiment, the base is sodium hydroxide.

The cationic carrier solution contains the charge neutralizing agent in an amount sufficient to neutralize a portion of the positive charge of the carrier molecules. This partial neutralization reduces charge associations and aggregation of the carrier molecules, while still maintaining an overall net positive charge associated with the carrier molecules (so that they are able to electrostatically bind negatively charged polynucleotides). In one embodiment of the invention, the charge neutralizing agent is added to the carrier solution in an amount sufficient to neutralize about 5 to 20% (e.g., about 10%) of the positive charge of the carrier molecules. The charge neutralizing agent may be added to the carrier solution before, after or concurrently with the charge shielding agent.

When using a base as the charge neutralizing agent, the carrier solution can be prepared with a concentration of base (e.g., NaOH) of about 10–1000 mM, preferably about 10–100 mM, more preferably about 50–70 mM, and most preferably about 59 mM, for carrier solutions containing carrier molecules at a concentration of about 0.5–20 mg/mL, preferably about 3–7 mg/mL, more preferably about 5–6 mg/mL, and most preferably about 5.6 mg/mL, respectively. The carrier solution can then be mixed vigorously to promote disaggregation of molecular carrier aggregates.

III Formation Of Molecular Complexes Containg Genes Encoding Interferon

Following formation of the carrier molecule of the molecular complex of the invention, the gene encoding IFN (e.g., in an expression plasmid) is linked to the carrier so that (a) the gene is sufficiently stable (either in vivo, ex vivo, or in vitro) to prevent significant uncoupling of the gene extracellularly prior to internalization by the target cell, (b) the gene is released in functional form under appropriate conditions within the cell, (c) the gene is not damaged and (d) the carrier retains its capacity to bind to cells. Generally, the linkage between the carrier and the gene is noncovalent. Appropriate noncovalent bonds include, for example, electrostatic bonds, hydrogen bonds, hydrophobic bonds, anti-polynucleotide antibody binding, linkages mediated by intercalating agents, and streptavidin or avidin binding to polynucleotide-containing biotinylated nucleotides. However, the carrier can also be directly (e.g., covalently) linked to the gene using, for example, chemical cross-linking agents (e.g., as described in WO-A-91/04753 (Cetus Corp.), entitled "Conjugates of Antisense Oligonucleotides and Therapeutic Uses Thereof").

The gene encoding IFN (e.g., in a vector) is combined (and allowed to equilibrate) with the carrier solution to form substantially disperse and soluble polynucleotide-carrier complexes. The gene is combined with the carrier solution so that the polynucleotide-carrier solution contains a final concentration of charge shielding agent and, optionally, charge neutralizing agent which does not damage or induce any substantial conformational change (e.g., denature) in the polynucleotide (i.e., the IFN gene) so that it remains substantially functional and in a form suitable for complexing with the carrier molecules. Generally, this corresponds to a final concentration of charge shielding agent (e.g., salt) of less than 1.0 M, preferably less than 0.75 M, and most preferably less than 0.5 M (e.g., about 0. 15–0.5 M), and a concentration of charge neutralizing agent of less than 10 mM, preferably less than 4.0 mM, and most preferably about 2.0 mM.

In one embodiment, the polynucleotide is diluted, for example, with nanopure water, prior to (or concurrently with) being combined with a carrier solution to a concentration which, when combined with the carrier solution, results in the desired final concentration of charge shielding agent (e.g., salt) and charge neutralizing agent (e.g., base). When adding the polynucleotide to a carrier solution containing a salt (e.g., NaCl) as the charge shielding agent, the polynucleotide can be diluted to a concentration which results in a final salt concentration (i.e., after mixing with carrier solution) of less than 1.0 M, preferably less than 0.5 M, more preferably about 0.15–0.5 M and most preferably about 0.3 M (about two times physiological). At this concentration of salt, the carrier molecules maintain a high level of dispersity and the polynucleotide remains functional.

If the carrier solution contains a charge neutralizing agent (e.g., a base), along with the charge shielding agent, then the final concentration of charge neutralizing agent in the carrier solution, following addition of the polynucleotide, should also be a concentration which does not substantially damage, alter, or inhibit the function of the polynucleotide. For example, when using a base as the charge neutralizing agent, the polynucleotide-carrier solution can contain a final base concentration of less than 50 mM, preferably less than 10 mM, more preferably less than 4.0 mM (e.g., about 1.0–4.0 mM), and most preferably about 2.0 mM.

In a preferred embodiment of the invention, the final solution in which the polynucleotide-carrier complexes are formed has (a) a carrier molecule concentration of about 3.0–7.0 mg/mL, preferably about 5.0–6.0 mg/mL, (b) a salt concentration of about 0.15–0.5 M, preferably about 0.3 M, (c) a base concentration of about 1.0–4.0 mM, preferably about 2.0 mM and (c) an appropriate final concentration of DNA (e.g., 10 µg/mL).

The polynucleotide (i.e., the IFN gene) is combined with the carrier solution in an amount appropriate to form stable complexes which remain soluble in solution. Generally, the polynucleotide is added to the carrier solution in a weight to weight (w:w) ratio (polynucleotide to carrier) of about 1:0.2–1:20, (e.g., about 1:1–1:10, or about 1:1.5–1:5). Complexes formed with these weight ratios (polynucleotide to carrier) have corresponding charge neutralization ratios (i.e., percent neutralization of negatively charge polynucleotide by positively charged carrier) of about 10–1000% (e.g., about 50–500%, or about 75–250%), respectively.

The performance of a given polynucleotide-carrier complex can be affected by the level of polynucleotide charge neutralization in the complex. The optimal level of polynucleotide charge neutralization for a given complex containing a gene encoding IFN can depend on the nature of the IFN gene (e.g., what kind of vector it is in) and the size and charge of the particular cationic carrier molecule used. While appropriate levels of polynucleotide charge neutralization for such complexes generally fall within the ranges provided above, the optimal level for a given IFN gene complex can be determined empirically. For example, a series of preparations can be made for a particular IFN gene complex each with varying degrees of polynucleotide charge neutralization. The performance of these samples can then be tested by, for example, measuring levels of IFN expression obtained with each sample either in vitro or in in vivo expression assays (e.g., ELISA), as described in the following examples.

Following formation of the polynucleotide (IFN gene)-carrier complex, the complex can, optionally, be extruded through an appropriate filter prior to being administered to cells (either in vitro or in vivo). The term "extruded", as used herein, means passage of the complexes through a filtering apparatus, followed by collection of the filtered product. Extrusion of complexes can (1) decrease the size of the complexes so that they are more easily internalized by target cells, (2) increase the homogeneity of the complexes, and (3) improve the performance of the complexes, as measured by IFN expression levels. While any extrusion apparatus which diminishes larger complexes and increases the proportion of smaller, more homogenous complexes may be used, a preferred apparatus for extruding complexes is a 50 nm filter attached to an Emulsi-Flex-C5 (Avestin, Inc. Ottawa, Canada).

V Administration Of Molecular Complexes Containing Genes Encoding Interferon

The soluble molecular complex of the invention can be used to deliver genes encoding IFN either in vitro or in vivo to selected cells, and to obtain expression of IFN in the cells.

In one embodiment, the complex is contacted (e.g., incubated) with a target cell in culture in an appropriate medium under conditions conducive to endocytotic uptake by the cells.

In another embodiment, the complex is administered in vivo to a subject in a pharmaceutically acceptable carrier. The term "pharmaceutically acceptable carrier", as used herein, is intended to include any physiologically acceptable carrier for stabilizing polynucleotide-carrier complexes of the present invention for administration in vivo, including, for example, saline and aqueous buffer solutions, solvents, dispersion media, antibacterial and antifungal agents, isotonic and absorption delaying agents, and the like. The use of such media and agents for pharmaceutically active substances is well known in the art. Except insofar as any conventional media is incompatible with the polynucleotide-carrier complexes of the present invention, use thereof in a therapeutic composition is contemplated.

In all cases, the pharmaceutical composition must be sterile and must be fluid to the extent that easy syringability exists. It must be stable under the conditions of manufacture and storage and must be preserved against the contaminating action or microorganisms such as bacteria and fungi. Protection of the polynucleotide-carrier complexes from degradative enzymes (e.g., nucleases) can be achieved by including in the composition a protective coating or nuclease inhibitor. Prevention of the action of microorganisms can be achieved by various anti-bacterial and anti-fungal agents, for example, parabens, chlorobutanol, phenol, ascorbic acid, thimerosal, and the like.

Molecular complexes of the invention may be administered in vivo by any suitable route of administration. The appropriate dosage may vary according to the selected route of administration. The complexes are preferably injected intravenously in solution containing a pharmaceutically acceptable carrier, as defined herein. Sterile injectable solutions can be prepared by incorporating the polynucleotide-carrier complexes in the required amount in an appropriate buffer with one or a combination of ingredients enumerated above, as required, followed by filtered sterilization. Other suitable routes of administration include intravascular, subcutaneous (including slow-release implants), topical and oral.

Appropriate dosages may be determined empirically, as is routinely practiced in the art. Mice can be administered dosages of up to 1.0 mg of polynucleotide per 20 g of mouse, or about 1.0 mL of complex per 1.4 mL of mouse blood.

This invention is illustrated further by the following examples which should not be construed as further limiting the subject invention. The contents of all references and published patent applications cited throughout this application are hereby incorporated by reference.

EXAMPLE 1

Preparation of Plasmids Encoding IFN-α

Various expression plasmids were prepared as follows using the human IFN-α2b clone, pALCA1SIFN, obtained from the American Type Culture Collection in Rockville, Md. (ATCC 53369). This clone encodes human IFN-α2b having the amino sequence shown in FIG. 11 (Streuli et al. (1980) *Science* 209:1343–1347). A map of each plasmid is shown in FIGS. 3–8.

pJ7ΩIFNα: Plasmid pJ7ΩIFNα was prepared by cloning a 991 bp Sal I to Eco RI fragment of pALCA1SIFN into the Sal I to Eco RI sites of vector pJ7Ω (Morgenstern et al. (1990) *Nucl. Acids Res.* 18(4):1068). The resulting plasmid, pJ7ΩIFNα, contains the human IFN-α2b gene expressed by the CMV promoter and flanked 3' of the gene by the SV40 small t intron and SV40 polyadenylation sequence.

pJ7ΩhIFNα: Plasmid pJ7ΩhIFNα was prepared identically to plasmid pJ7ΩIFNα except that a point mutation (i.e., modification of three nucleotides) flanking the AUG initiation codon was made as described in Kozak et al. (1986) *Cell* 44:283–292 to match the known 5' consensus sequence for IFN-α2b gene (see also WO 86/06097).

pJ7ΩhIFNαSB: Plasmid pJ7ΩhIFNαSB was prepared identically to plasmid pJ7ΩhIFNα except that the CMV promoter/enhancer was replaced by the thyroxin binding globulin (TBG) promoter (Hayashi et al. (1993) *Molec. Endocrinol.* 7:1049–1060) coupled to two copies of the alpha-1 microglobulin/bikunin enhancer (Rouet et al. (1992) *J. Biol. Chem.* 267:20765–20773) followed by a β-globin (IVS) and the SV40 small t intron (IVS) was placed immediately downstream of the IFN gene.

pJ7ΩhIFNα-nonSB: Plasmid pJ7ΩhIFNα-nonSB was prepared identically to plasmid pJ7ΩhIFNαSB except a region of the 3' non-coding sequence of the human IFN-α2b gene (Streuli et al. (1980), supra.) extending from the EcoRI restriction site to the SPE-1 restriction site of the IFN gene was removed.

pSVIFNα: Plasmid pSVIFNα was prepared by cloning a 991 bp Sal I to Eco RI fragment of pALCA1SIFN into the Sal I to Bgl II sites of plasmid pSV $HBV_2$ (Merwin et al. (1949) *Bioconjugate Chem.* 5:612–620) in which the Bgl II site was blunted, and on to which Eco RI linkers were ligated, prior to ligation of the pALCA1SIFN fragment. The resulting plasmid, pSVIFNα, contains the human IFN-α2b gene expressed by the SV40 early promoter and terminated 3' of the gene by the SV40 small t intron and SV40 polyadenylation sequence.

pSVIFNαRV: Plasmid pSVIFNαRV was prepared by cloning a 991 bp Sal I to Eco RI fragment of pALCA1SIFN into the Sal I to Eco RV sites of plasmid pSV $HBV_2$ (Merwin et al. (1994) *Bioconjugate Chem.* 5:612–620) in which the Eco RI site of the pALCA1SIFN fragment was blunted prior to ligation. The resulting plasmid, pSVIFNαRV, contains the human IFN-α2b gene expressed by the SV40 early promoter and flanked 3' of the gene by HBV sequences containing Enhancer 1 and Enhancer 2 sequences, the X gene, and the HBV polyadenylation sequence, followed by the SV40 small t intron and the SV40 polyadenylation sequence.

EXAMPLE 2

Formation of Targeted Complexes Containing Plasmids Encoding Human IFN-α2b

Targeted molecular complexes containing each of the human IFN-α2b expression plasmids prepared in Example 1 were formed as follows:

Conjugates of ASOR and poly-L-lysine were prepared by carbodiimide coupling similar to that reported by McKee et al (1994) *Bioconjugate Chem.* 5: 306–311. In brief, ASOR, 26 kD poly-L-lysine and EDC in a 1:1:0.5 mass ratio were reacted as follows. EDC (dry) was added directly to a stirring aqueous ASOR solution. 26 kD Polylysine was added and the reaction mixture was adjusted to pH 5.5–6.0 and stirred for two hours at ambient temperature. ASOR concentration was 5 mg/mL in the final reaction conditions. The reaction was quenched by addition of $Na_3PO_4$ (200 mM, pH 11) to a final concentration of 10 mM. The conjugate was first purified on a Fast Flow Q Sepharose anion exchange chromatography column (Pharnacia) eluted with 50 mM Tris, pH 7.5, and then dialyzed against ultra-pure water.

The ASOR-poly-L-lysine conjugate, at a concentration of about 5.6 mg/mL, was aliquoted into a reaction vessel to which was added an amount of 5 M NaCl to obtain a final concentration of about 4.7 M NaCl and an amount of 1 M NaOH to obtain a final concentration of about 59 mM NaOH. The solutions were mixed vigorously.

Each plasmid prepared in Example 1 (i.e., pJ7ΩIFNα, pJ7hIFNα, pJ7ΩhIFNαSB, pJ7ΩhIFNα-nonSB, pSVIFNα, and pSVIFNαRV) in 10 mM Tris-HCI, 1 mM EDTA buffer was diluted by adding nanopure water and then combined with the ASOR-poly-L-lysine conjugate solution to achieve a final concentration of 300 mM NaCl and 2 mM NaOH, and a final concentration of plasmid of 10 μg/ml.

Complexes were formed with a ratio of DNA to carrier sufficient to neutralize 50% of the negative charge of the DNA. To determine this ratio, an aliquot of the purified dialyzed conjugate solution was lyophilized, weighed and dissolved in ultra-pure water at a specific concentration (w/v). Since polylysine has minimal absorbance at 280 nm, the ASOR component of the conjugate (w/v) was calculated using the extinction co-efficient at 280 nm. The composition of the conjugate was estimated by comparison of the concentration of the conjugate (w/v) with the concentration of ASOR (w/v) as determined by UV absorbance. The difference between the two determinations was attributed to the polylysine component of the conjugate. The ratio of conjugate to DNA (w:w) necessary for charge neutralization was then calculated using the determined cationic composition.

The materials and methods used in the protocols described above are as follows: Protamine, Poly-L-lysine (26 kD; mean MW) was purchased from Sigma Chemical Co., St. Louis, Mo. 1-[3-(dimethylamino)-propyl]-3-ethylcarbodiimide (EDC) was purchased from Aldrich Chemical Co, Milwaukee, Wis. Orosomucoid was purchased from Alpha Therapeutics, Los Angeles, Calif. Asialoorosomucoid (ASOR) was prepared from Orosomucoid (15 mg/ml) by hydrolysis with 0.1 N sulfuric acid at 76 ° C. for one hour. ASOR was purified from the reaction mixture by neutralization with 1.0 N NaOH to pH 5.5 and exhaustive dialysis against water at room temperature. ASOR concentration was determined using an extinction coefficient of 0.92 mL $mg^{-1}$, $cm^{-1}$ at 280 nm. The thiobarbituric acid assay of Warren (1959) *J. Biol. Chem.* 234: 1971–1975 was used to verify desialylation of the OR. ASOR prepared by the above method was determined to be 98% desialylated.

EXAMPLE 3

In Vivo Expression Assays Using Targeted Complexes Containing Plasmids Encoding Human IFN-α2b To study in vivo human IFN-α2b expression levels, duration and biological activity obtained following administration of the targeted molecular complexes formed in Example 2, assays were performed in mice as follows:

I. In Vivo Assays Demonstrating Long Term IFN Expression at Therapeutically Significant Levels A 1.0 ml dose of complex solution (pJ7ΩIFNα-P1-ASOR, pJ7ΩhIFNα-P1-ASOR, pJ7ΩhIFNαSB-P1-ASOR, pJ7ΩhIFNα-nonSB-P1-ASOR, pSVIFNα-P1-ASOR, and pSVIFNαRV-P1-ASOR at 17570 μg DNA/ml) was injected intravenously via the tail vein into adult (18–20 gm) female BALB/C mice. Two mice were injected per plasmids pJ7ΩIFN, pSVIFNα, and pSVIFNαRV, shown in FIGS. 1 and 2. Four mice were injected per plasmids pJ7ΩhIFNα, pJ7ΩhIFNαSB and pJ7ΩhIFNα-nonSB, shown in FIG. 9. Additional control mice received 1.0 ml injections of an identically formulated human growth hormone (hGH) plasmid-containing complex.

For complexes containing pJ7ΩIFNα, pSVIFNα, and pSVIFNαRV, blood samples were taken from the animals by retroorbital puncture at 24, 48 and 96 hours post-injection. For complexes containing pJ7ΩhIFNα, pJ7ΩhIFNαSB and pJ7ΩhIFNα-nonSB, blood samples were taken from the animals by the same method (i.e., retroorbital puncture) at 3, 6, 9, 12, 15, 18, 21, 24, 27, 30, 33, 36 and 39 days post-injection. Serum from samples were analyzed for human IFN-α2b protein by ELISA. The quantitative ELISA was performed using a human-specific IFN-α2 detection kit (Endogen catalog number EH-IFNA) according to the manufacturer's recommended protocol. This ELISA assay does not cross-react with murine interferons or other forms of human interferon. The results were compared to a standard curve to estimate the amount (pg/ml) of human IFN-α2b present in each sample. Control animals treated with hGH complex did not produce any measurable human IFN-α2b. The results are shown in FIGS. 1, 2 and 9.

FIG. 1 shows levels of human IFN-α2b expression in mice 24 hours following injection with each plasmid complex at a dose of 10 μg of plasmid complex per mouse. The highest expression (up to 175 pg/ml) was obtained for complexes containing pJ7ΩIFNα-P1-ASOR. The average expression for all three plasmid complexes was 85 pg/ml.

Figure 2:
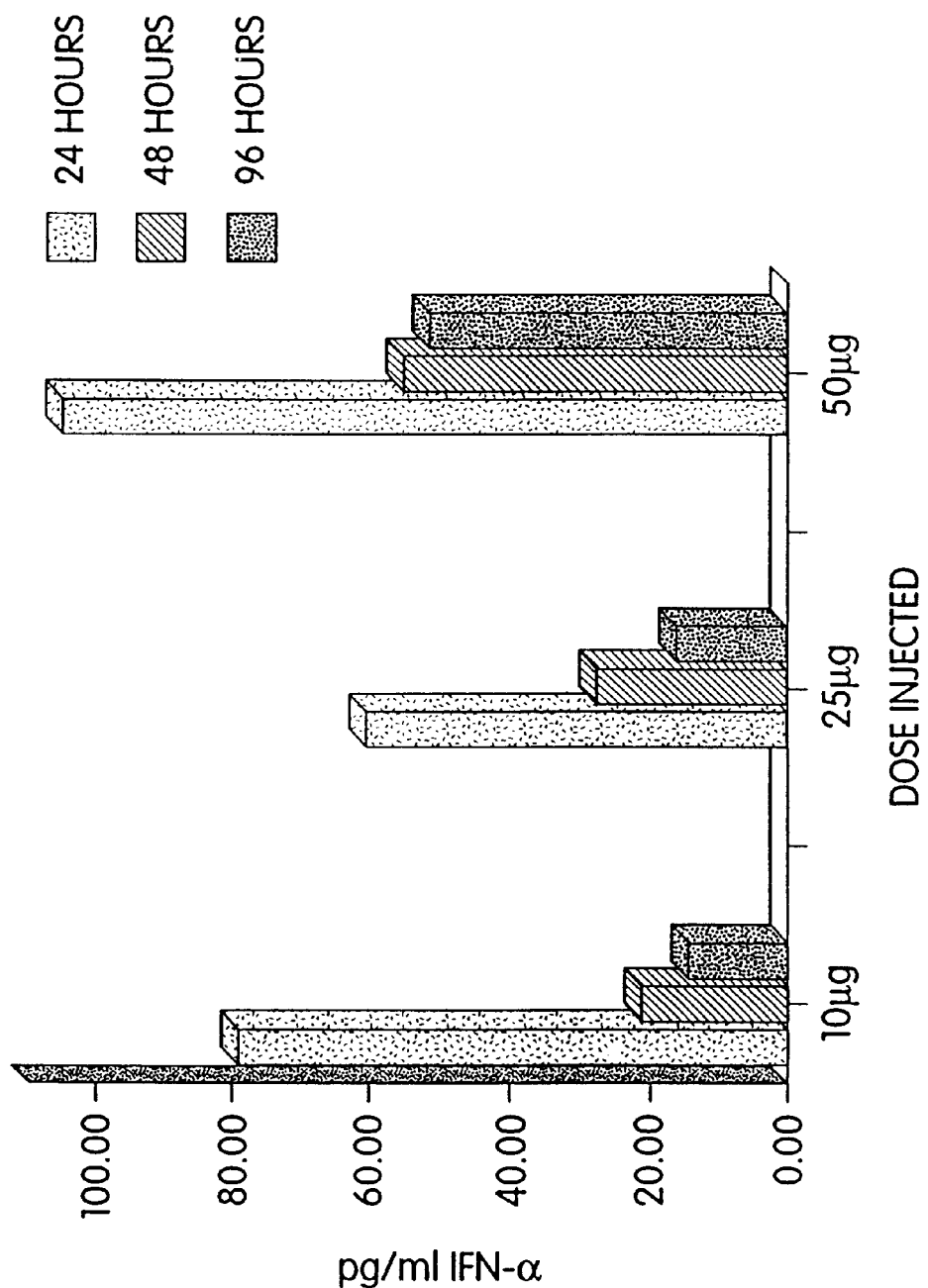
FIG. 2 is a graphic representation of IFN-$\alpha$ expression levels (pg/ml IFN-$\alpha$) in mice injected with various dosages (10 $\mu$g, 25 $\mu$g, and 50 $\mu$g) of plasmid pJ7$\Omega$IFN$\alpha$ encoding human IFN-$\alpha$2b. Expression levels were measured at 24, 48 and 96 hours post-injection. The plasmid was administered in the form of a targeted molecular complex made up of the plasmid complexed to a carrier molecule of polylysine and asialoorosomucoid which binds to the asialoglycoprotein receptor present on liver cells.
Figure 3:
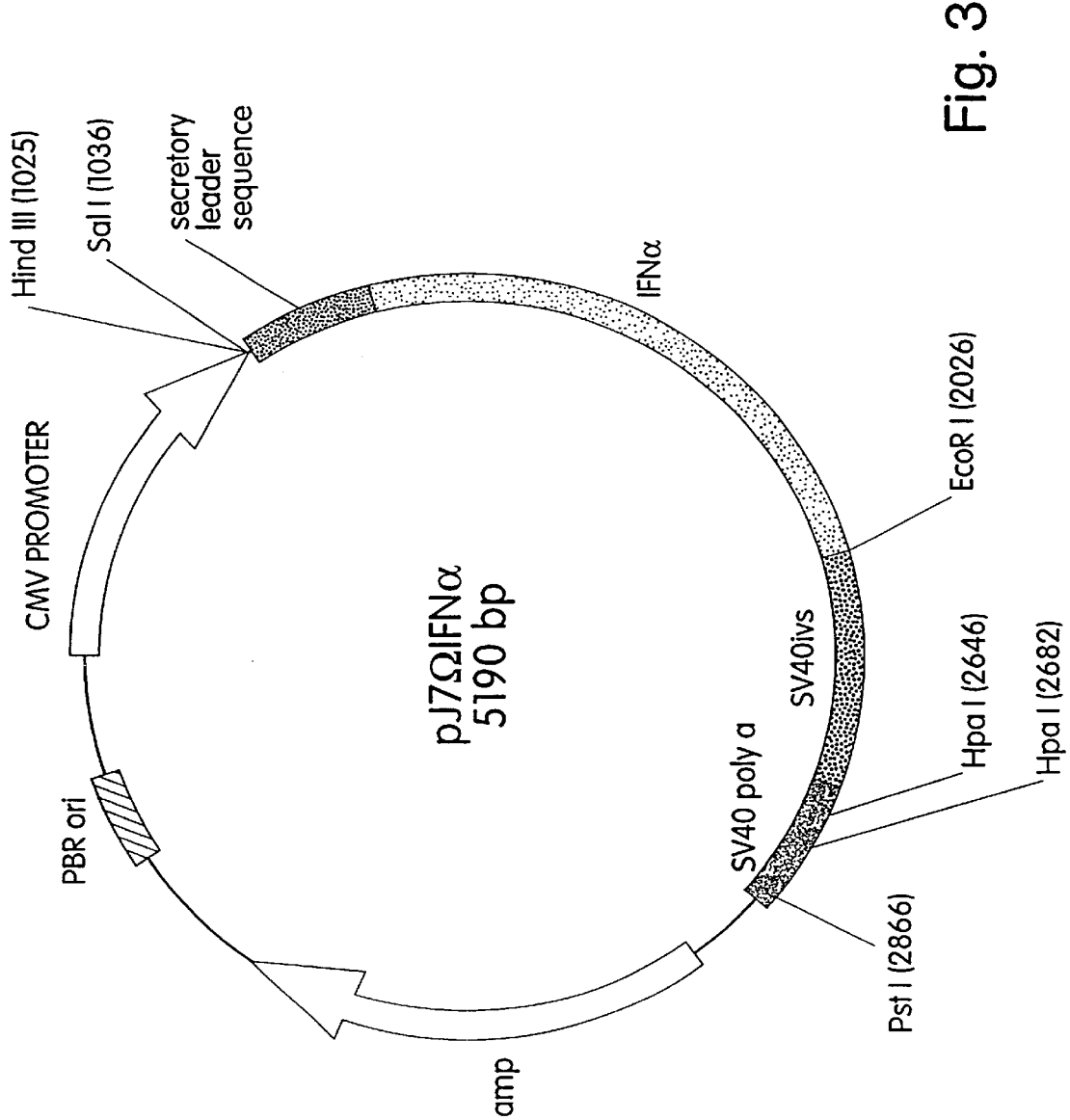
FIG. 3 shows a map of the expression plasmid, pJ7$\Omega$IFN$\alpha$, containing the human IFN-$\alpha$2b gene expressed by the CMV promoter followed downstream by the SV40 small t intron (IVS) and the SV40 polyadenylation signal.
Figure 4:
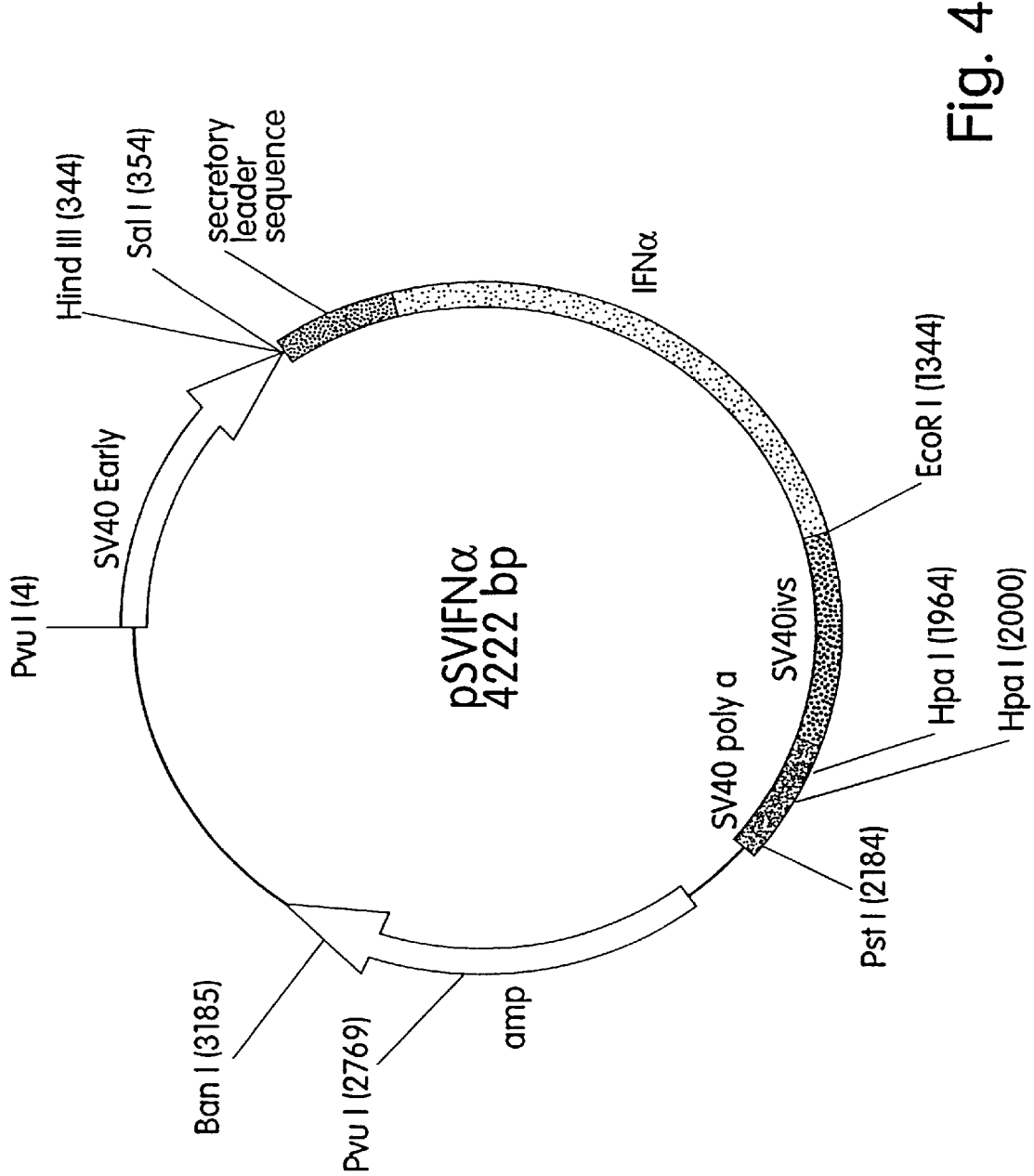
FIG. 4 shows a map of the expression plasmid, pSVIFNα, containing the human IFN-α2b gene expressed by the SV40 early promoter followed downstream by the SV40 small t intron (IVS) and the SV40 polyadenylation signal.
Figure 5:
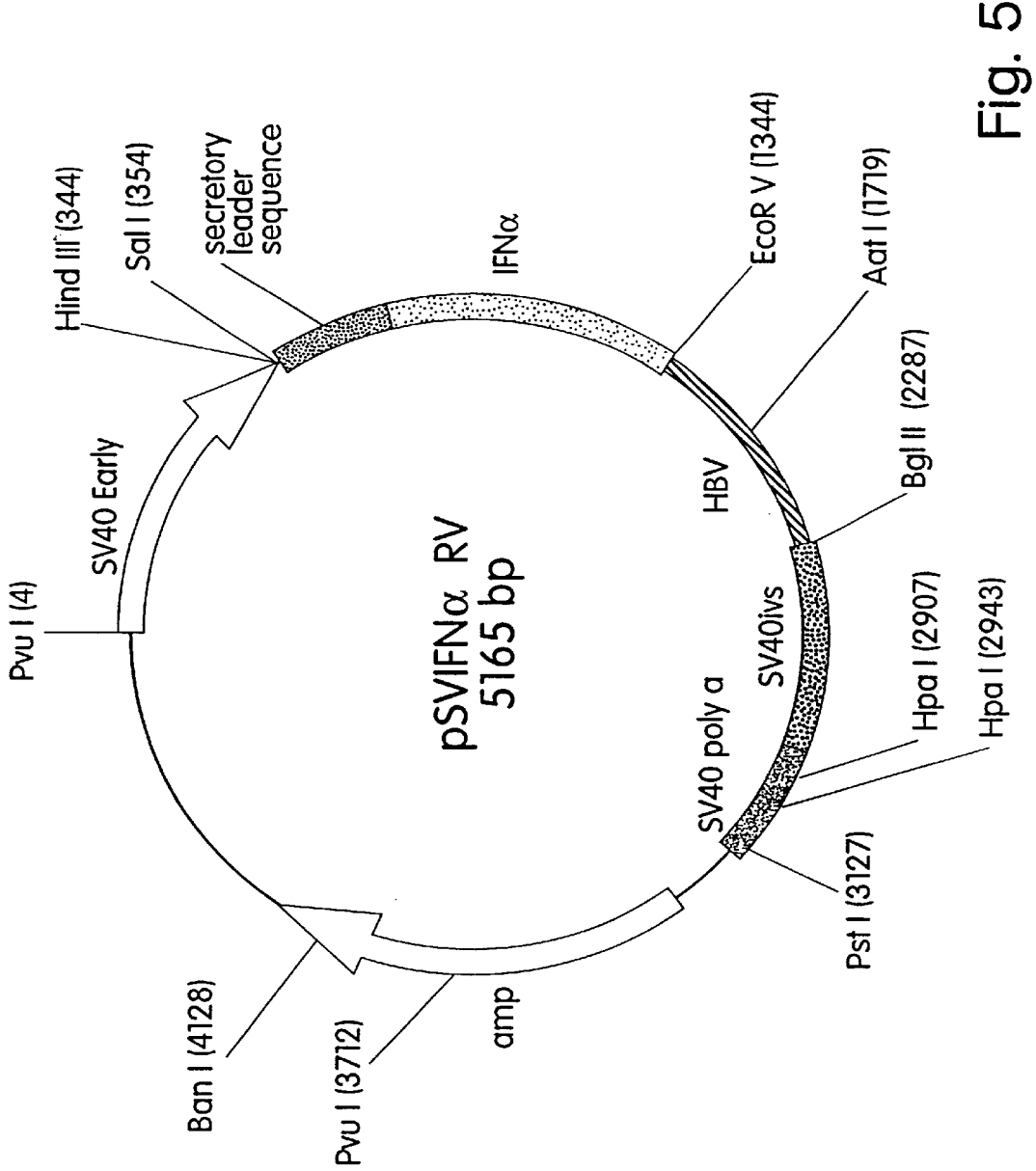
FIG. 5 shows a map of the expression plasmid, pSVIFNαRV, containing the human IFN-α2b gene expressed by the SV40 early promoter followed downstream by HBV sequences containing (a) enhancer I and II, (b) the X gene, and (c) the HBV polyadenylation signal, followed downstream by the SV40 small t intron (IVS) and the SV40 polyadenylation signal.
Figure 6:
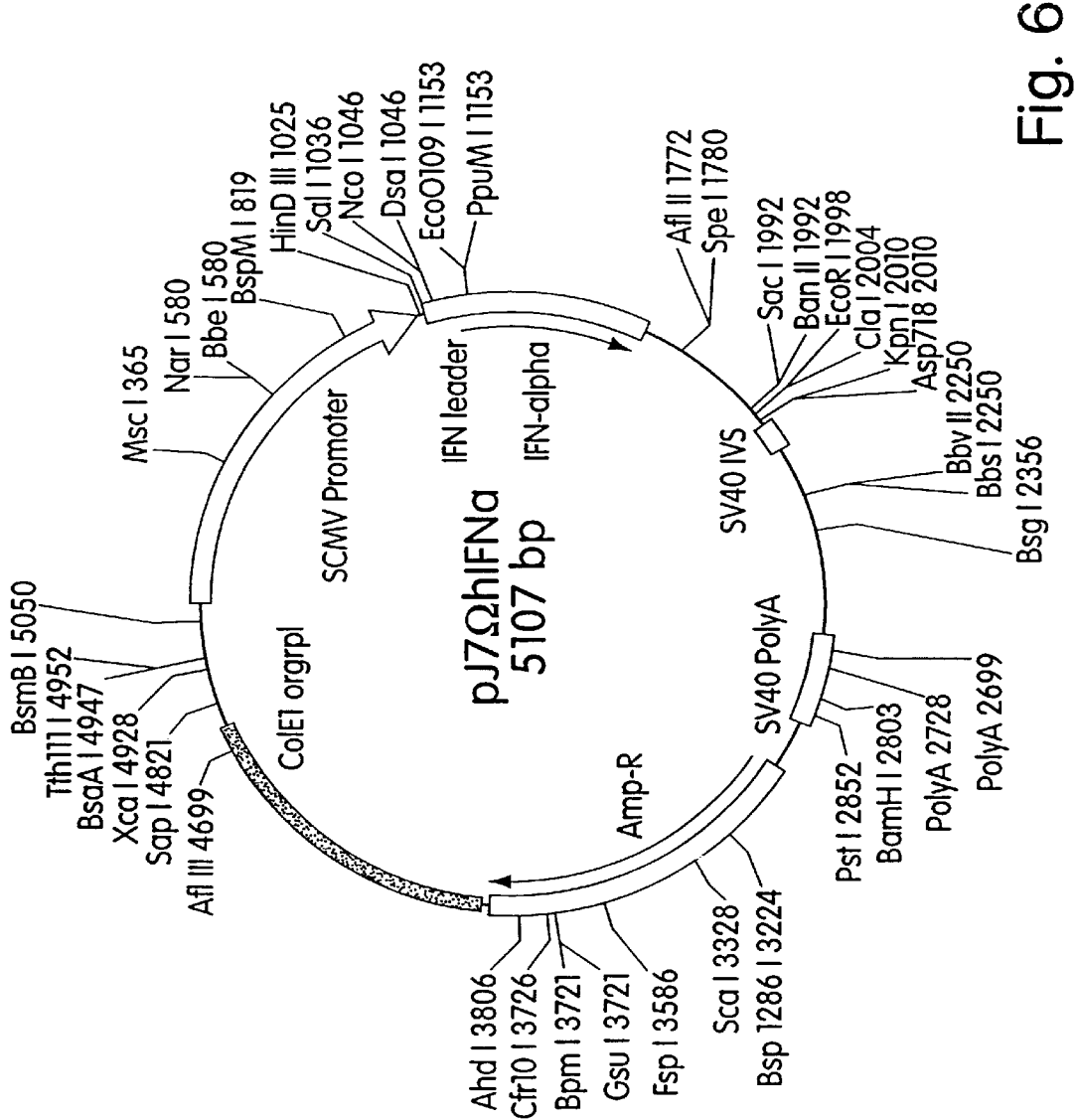
FIG. 6 shows a map of the expression plasmid, pJ7ΩhIFNα, containing the human IFN-α2b gene expressed by the CMV promoter/enhancer followed downstream by the SV40 small t intron (IVS) and the SV40 polyadenylation signal. The plasmid is identical to pJ7ΩIFNα (FIG. 3), except that the region flanking the AUG initiation codon is modified to optimize expression.
Figure 7:
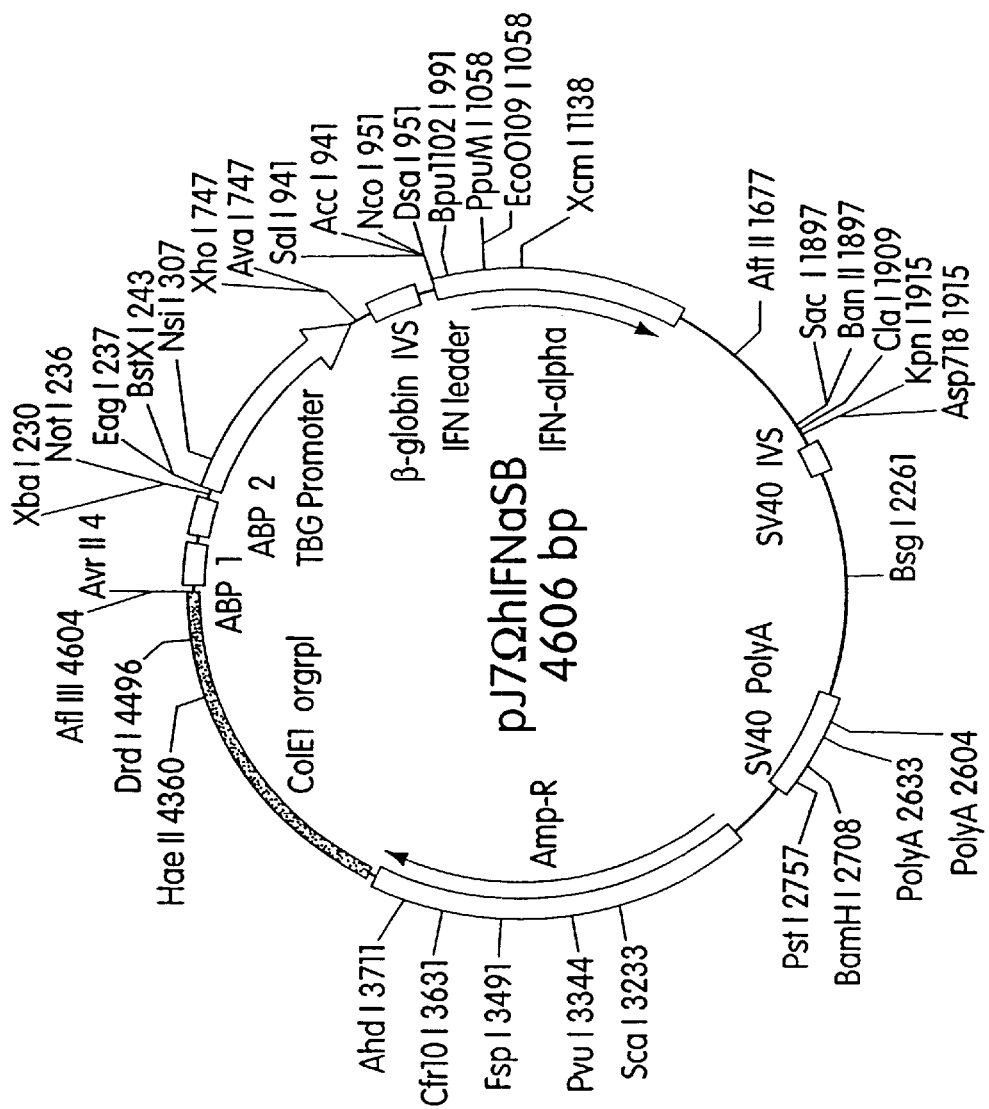
FIG. 7 shows a map of the expression plasmid, pJ7ΩhIFNαSB. The plasmid is identical to pJ7ΩhIFNα (FIG. 6), except that the CMV promoter/enhancer is replaced by the thyroxin binding globulin (TBG) promoter coupled to two copies of the alpha-1 microglobulin/bikunin enhancer. In addition, a β-globin (IVS) is located upstream of the interferon gene and the SV40 small t intron (IVS) is located immediately downstream of the interferon gene.
Figure 8:
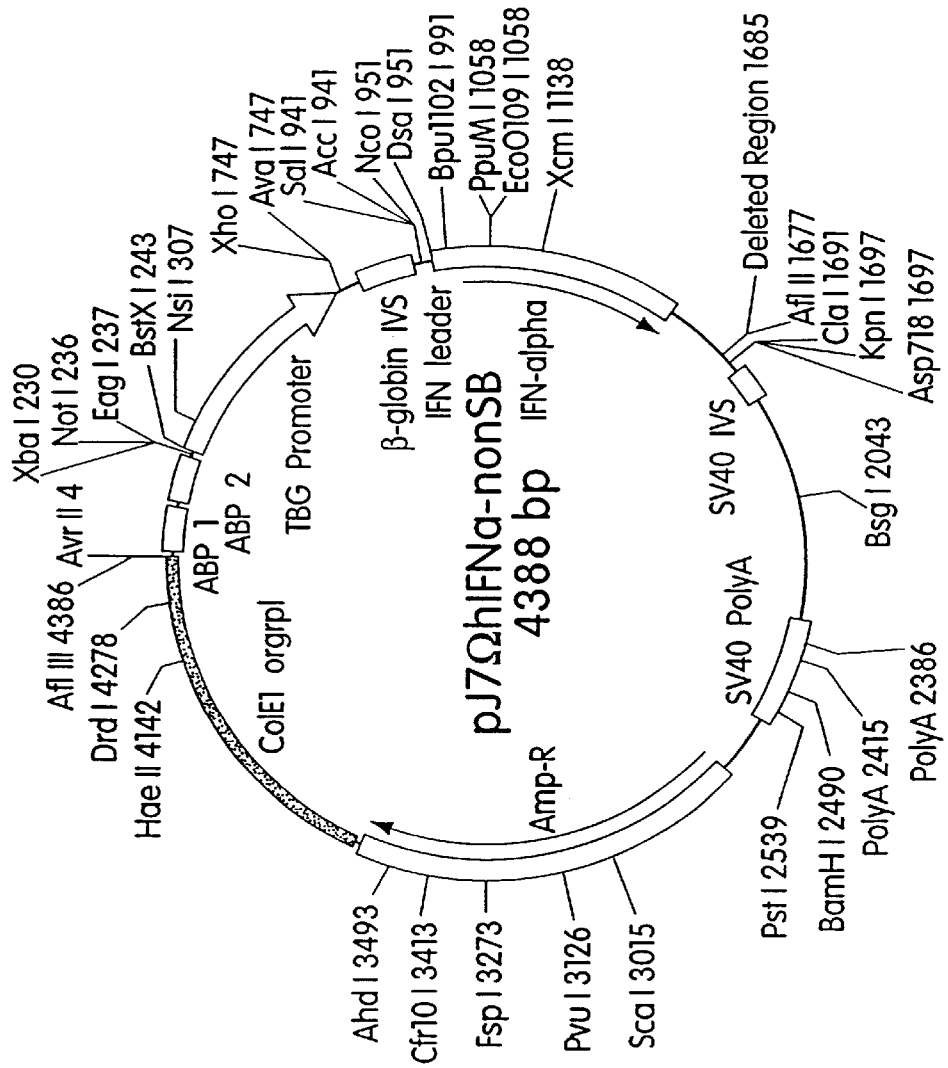
FIG. 8 shows a map of the expression plasmid, pJ7ΩhIFNα-nonSB. The plasmid is identical to pJ7ΩhIFNαSB shown in FIG. 5 except that a region of the 3' non-coding sequence of the IFN gene is absent.

FIG. 2 shows levels of human IFN-α2b expression in mice at 24, 48 and 96 hours post-injection with 10 μg, 25 μg, and 50μg of plasmid pJ7ΩIFN (as a complex). Dosages of 10 μg of plasmid resulted in expression levels ranging from 80 pg/ml at 24 hours to about 17 pg/ml at 96 hours. Dosages of 25 μg of plasmid resulted in expression levels ranging from about 65 pg/ml at 24 hours to about 19 pg/ml at 96 hours. Dosages of 50 μg of plasmid resulted in expression levels ranging from about 110 pg/ml at 24 hours to about 55 pg/ml at 96 hours.

Figure 9:
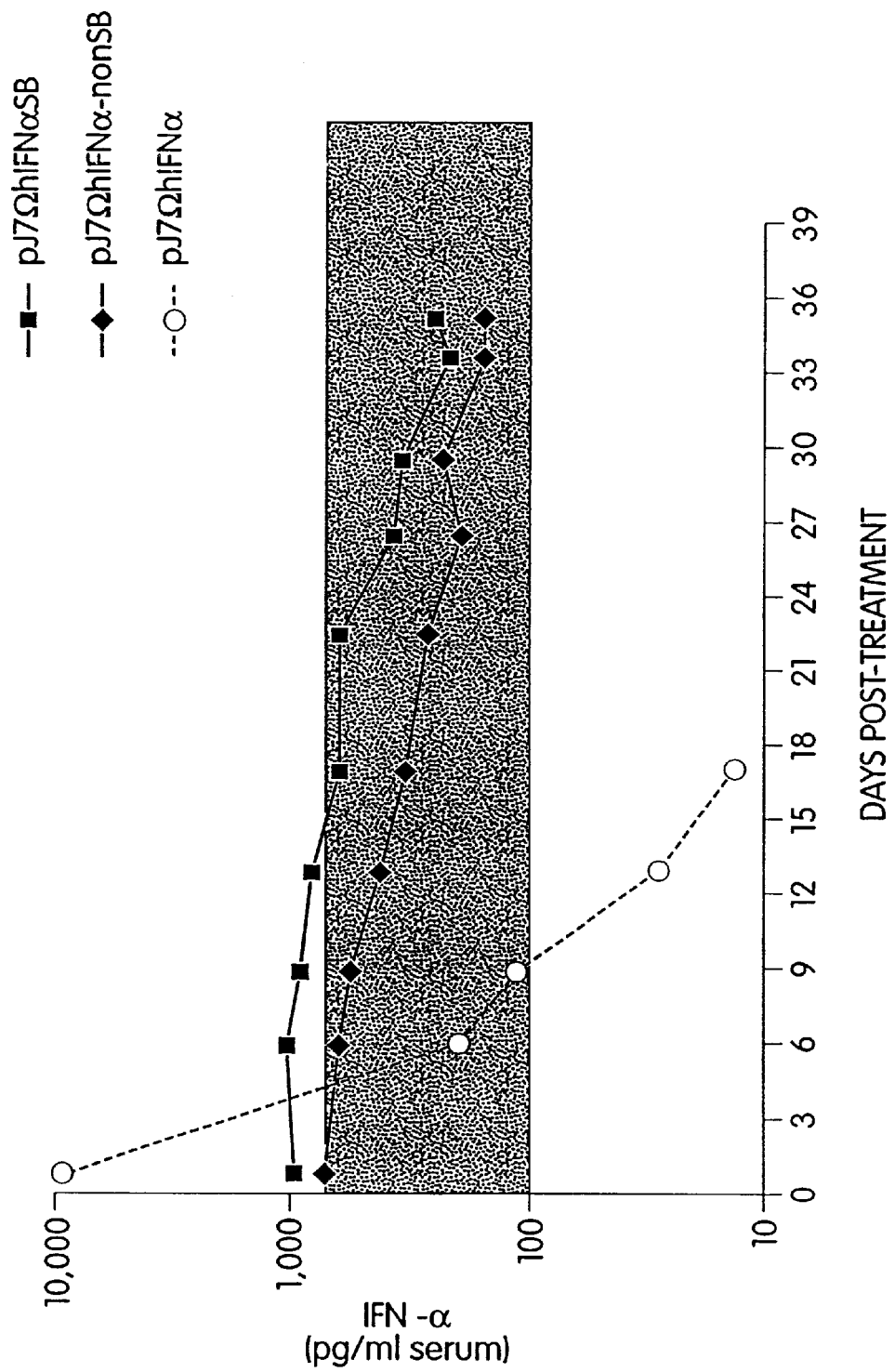
FIG. 9 is a graphic representation of IFN-α expression levels (pg/ml IFN-α) in mice injected with 10 μg of plasmids pJ7hΩIFNα, pJ7hΩIFNαSB and pJ7hΩIFNα-nonSB encoding human IFN-α2b. Each point on the graph represents the average of values obtained from four mice. Expression levels were measured every three days post-injection. The plasmids were administered in the form of a targeted molecular complex made up of the plasmid complexed to a carrier molecule of polylysine and asialoorosomucoid. Serum concentrations of IFN-α were measured by ELISA as described in the Exemplification. The shaded region of the graph shows the range of peak IFN-α serum concentrations in patients 4–12 hours after intramuscular injection.

FIG. 9 is a graphic representation of IFN-α2b expression in mice injected with 10 μg of plasmids pJ7ΩhIFNα, pJ7ΩhIFNαSB and pJ7ΩhIFNα-nonSB (as a complex). Expression levels were measured every three days post-injection up to 39 days. At days 1 and 2 post-injection, pJ7ΩhIFNα produced between 5,000 and 11,000 pg/ml of IFN-α2b with expression levels decreasing by day 18. With plasmids pJ7ΩhIFNαSB and pJ7ΩhIFNα-nonSB, peak serum concentrations of about 1,000 pg/ml were achieved and expression was sustained for greater than one month (up to at least 38 days) with only a modest downward trend.

Figure 10:
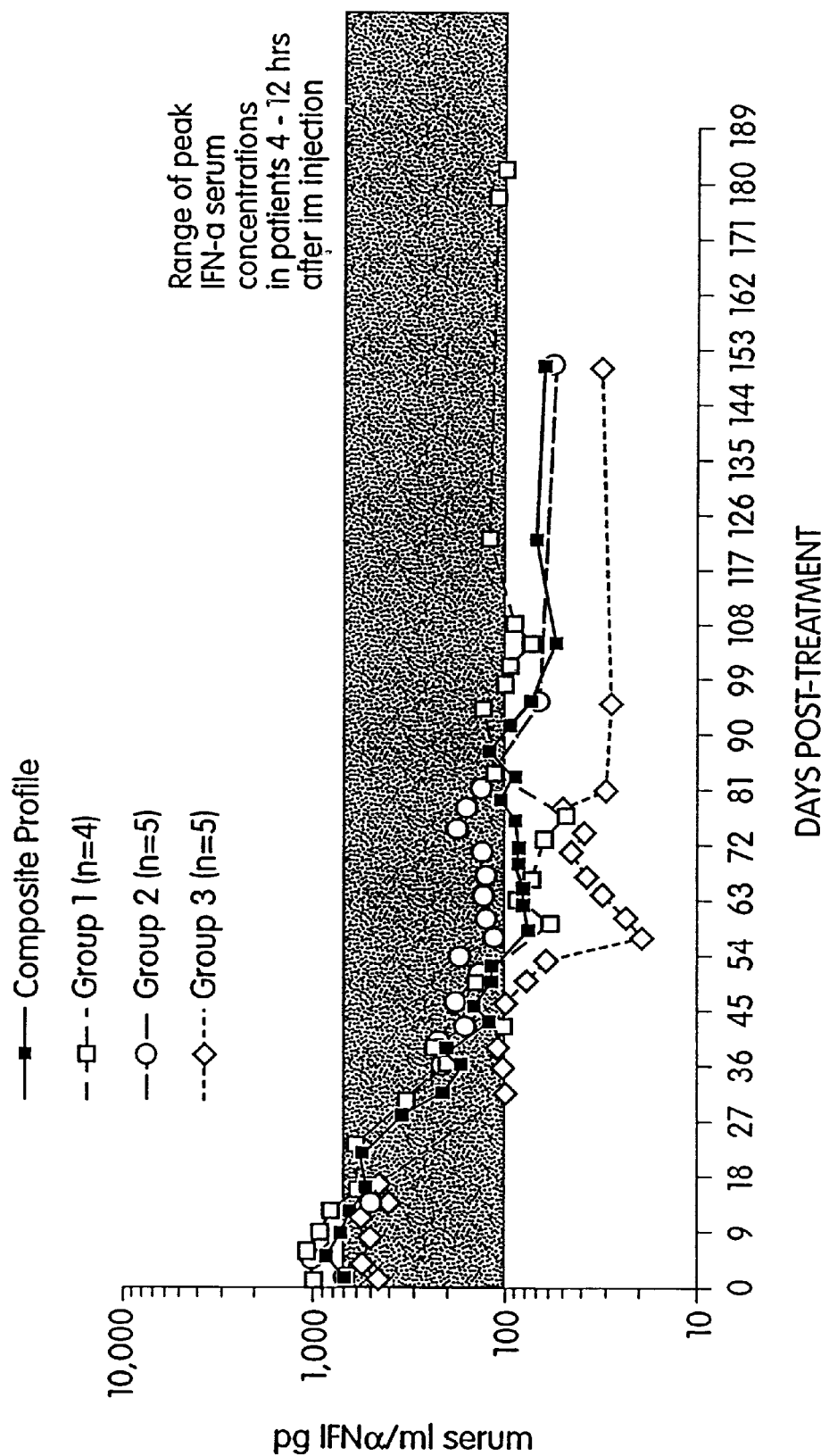
FIG. 10 is a graphic representation of IFN-α expression levels (pg/ml IFN-α) in mice injected with 10 μg of plasmid pJ7hΩIFNαSB encoding human IFN-α2b. Expression levels were measured at various time points post-injection out to 185 days. The number of mice used in each experimental group (Groups 1, 2 and 3) is listed in the legend as (n=). Groups 1 and 2 were administered plasmid in the form of a targeted molecular complex made up of the plasmid complexed to a carrier molecule of polylysine and asialoorosomucoid. Group 3 was administered plasmid in the form of a targeted molecular complex made up of the plasmid complexed to a carrier molecule of polylysine and lactose. The plot symbol for each group represents the average serum concentration at each time point for that group. The composite expression profile (heavy solid line) represents the average of values obtained from all three groups (total of 14 mice) up the last common time point (153 days). Serum concentrations of IFN-α were measured by ELISA as described in the Exemplification. The shaded region of the graph shows the range of peak IFN-α serum concentrations (100–600 pg/ml) in patients 4–12 hours after intramuscular injection with standard protein therapy for chronic HBV.
Figure 12A:
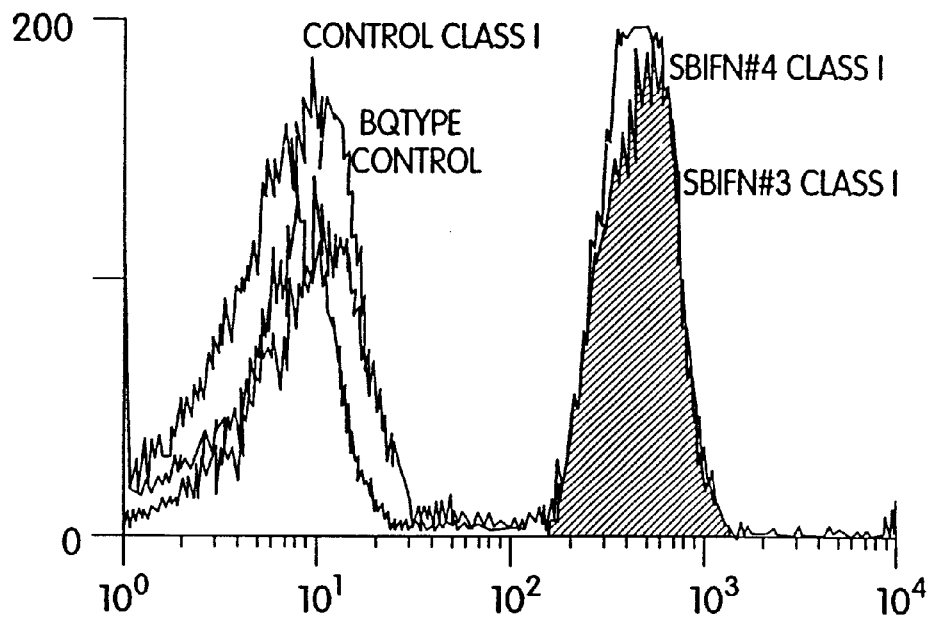
FIGS. 12A–12E show the increase in IFN-α activity of the IFN-2α-K121R125 hybrid protein (SEQ ID NO:7) shown in FIG. 11 as measured by increased MHC class I antigen induction in mice injected with plasmid encoding the hybrid. The plasmid encoding the hybrid was identical to plasmid pJ7hΩIFNαSB (FIG. 7) except that the human IFN-α2b coding sequence was modified to encode Lys (K) instead of Arg (R) at residue 121, and Arg (R) instead of Glutamine (Q) at residue 125. Mice were injected with 10 μg of plasmid in the form of a targeted molecular complex made up of the plasmid complexed to a carrier molecule of polylysine and asialoorosomucoid. At 10 days post-injection, the spleens were removed for FACS analysis of the isolated splenocytes. Panels A–E show the results of the FACS analysis. The shaded region of Panels B–E shows the rightward shift, indicating the increase in MHC class I antigen staining cells compared to control (Panel A), which occurs in mice injected with plasmid the IFN-2α-K121R125 hybrid protein.
Figure 12B:
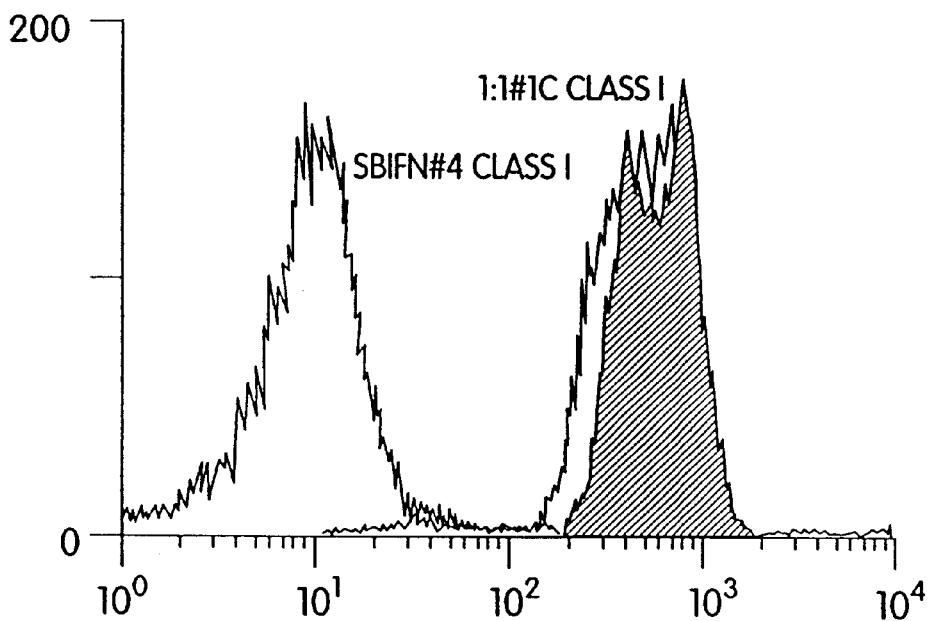
Figure 12C:
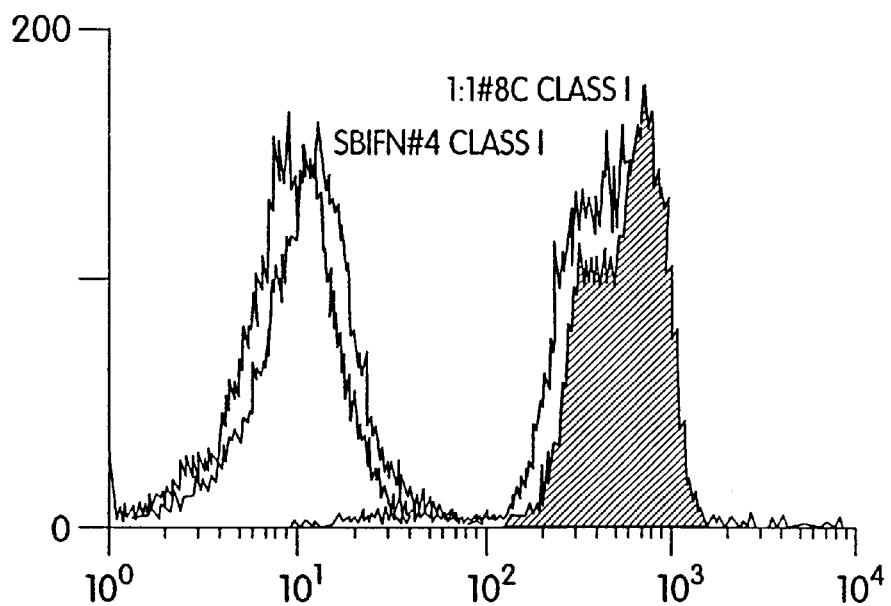
Figure 12D:
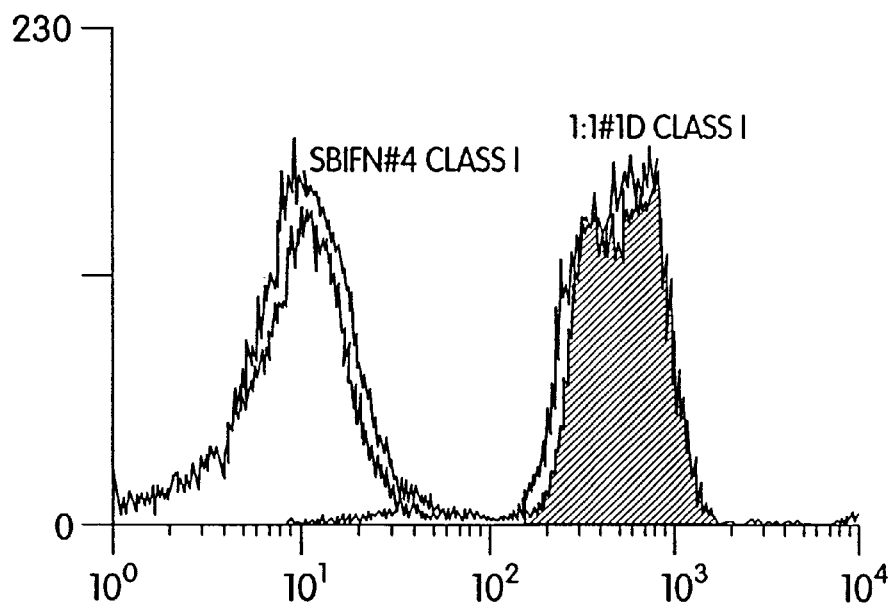
Figure 12E:
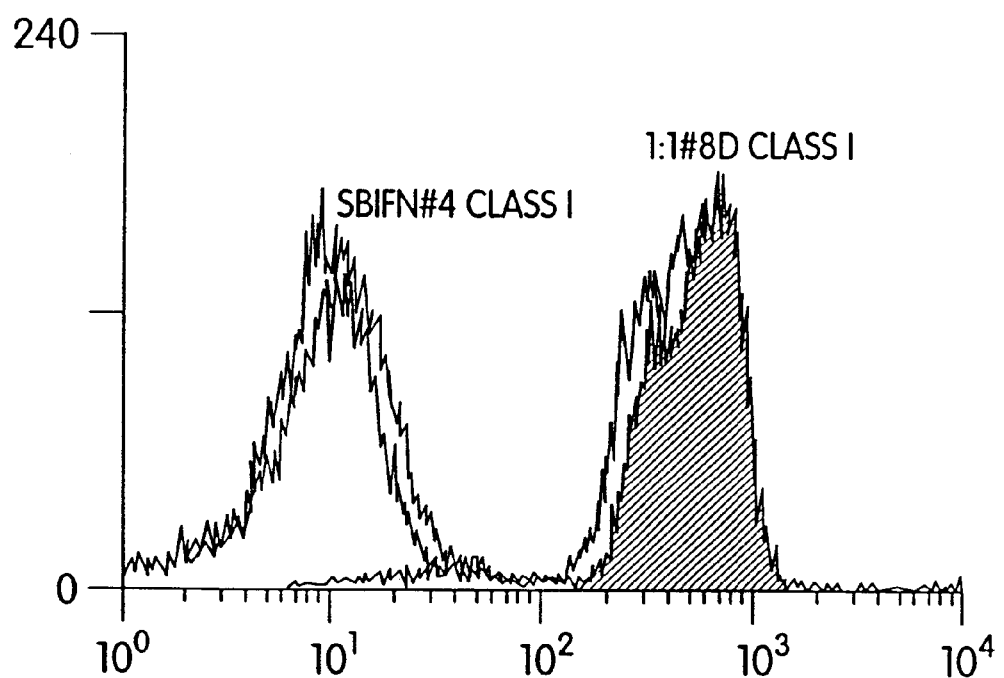

Measurements for expression of plasmid pJ7ΩhIFNαSB (i.e., serum levels of IFN-α2b) were continued through day 185 and, as shown in FIG. 10, expression was sustained with only a modest downward trend. Overall, these results demonstrate that unexpectedly long term in vivo expression of IFN can be achieved in animal models by way of IFN plasmid complexes of the invention. For example, in human patients treated with standard dosages of IFN-α protein to treat chronic HBV, IFN-α serum concentrations fall rapidly such that they are usually undetectable 16 hours or so after injection ("Drug Facts and Comparisons," supra.).

In addition, the results shown in FIGS. 9 and 10 show that long term in vivo IFN expression can be achieved in animal models at levels which are well within the range shown to be therapeutically effective in humans. In particular, the shaded regions of FIGS. 9 and 10 show the range of peak IFN-α serum concentrations (100–600 pg/ml) in patients 4–12 hours after intramuscular injection with standard protein therapy for chronic HBV (see e.g., "Drug Facts and Comparisons", 1992 Edition, eds. Olin, B. R. et al., St. Louis, Mo., pp. 2445–2460). In FIG. 9, IFN-α2b expression levels remained within the therapeutic range for humans up to the last data point taken (38 days). In FIG. 10, IFN-α2b expression levels for the composite of all three test Groups (1–3) remained within the therapeutic range for humans up to day 56 and again between days 81–98. Group 1 produced expression levels within the therapeutic range for humans continuously up to day 90. Group 2 produced expression levels within the therapeutic range for humans until day 54 and then again between days 80–185.

Overall, these results demonstrate that long-term in vivo IFN expression can be achieved in animal models at therapeutically significant levels by way of the present invention.

II. Assays Demonstrating In Vivo Expression of Biologically Active IFN

To assay for biological activity of IFN-α2b protein recombinantly expressed in vivo in mice injected with plasmid complexes of the invention, the following study was performed.

Plasmid pJ7hΩIFNαSB (FIG. 7) was modified using standard PCR-mediated site-directed mutagenesis to change the coding sequence for human IFN-α2b (SEQ ID NO:1) so as to encode Lys (K) instead of Arg (R) at residue 121, and Arg (R) instead of Glutamine (Q) at residue 125, the amino acids naturally found at those positions in human IFN-α1 (SEQ ID NO:2) (FIG. 11a). This change has been shown to increase biological activity of human IFN-α2 expressed in mice (Weber et al. (1987) EMBO J. 6:591–598) (FIG. 11b). Thus, as modified, plasmid pJ7hΩIFNαSB encoded a human IFN-α2b protein "hybrid" having the amino acid sequence shown in FIG. 11b corresponding to IFN-α2-K121R125 (SEQ ID NO:13).

Biological activity of human IFN-α2 expressed in control (i.e., unmodified pJ7hΩIFNαSB) and test (i.e., modified pJ7hΩIFNαSB) mice was measured by increased MHC class I antigen. Induction of MHC class I is an art recognized marker for the biological activity of IFN (Pestka et al. (1987) Ann. Rev. Biochem. 56:727–777). Mice were injected via tail vein with 10 μg of plasmid in the form of a targeted molecular complex prepared as described in Example 2. At 10 days post-injection, the spleens were removed for FACS analysis of the isolated splenocytes. Splenocytes from mice injected with unmodified plasmid complex containing pJ7hΩIFNαSB (i.e., encoding human IFN-α2b having the IFN-α2 sequence shown in FIG. 11(a)) were used as a control (Panel A).

Panels A–E show the results of the FACS analysis. Panel A (control) showed no alteration in the population of class 1 antigen staining spleen cells from two mice. However, Panels B–E (shaded areas) showed a distinct increase (rightward shift) in MHC class I antigen staining cells compared to Panel A (control). The curve from Panel A is superimposed onto the curves of Panels B–E so that the rightward shift of the curves of Panels B–D can be better seen. A similar amount of MHC class I antigen induction was also observed in mice treated with a total of 100,000 IU of murine IFN-α protein (by way of 5 intramuscular injections of protein over 2.5 days).

Overall, these results demonstrate that IFN expressed in vivo by way of the methods and plasmid complexes of the present invention possesses biologically activity.

EQUIVALENTS

Although the invention has been described with reference to its preferred embodiments, other embodiments can achieve the same results. Those skilled in the art will recognize or be able to ascertain using no more than routine experimentation, numerous equivalents to the specific embodiments described herein. Such equivalents are considered to be within the scope of this invention and are encompassed by the following claims.

What is claimed is:

1. A method of treating hepatitis infection in a mammalian subject comprising administering to the subject a molecular complex comprising a gene encoding interferon-α releasably linked to a conjugate of a cationic agent which binds the gene and a ligand which binds to the asialoglycoprotein receptor on the surface of liver cells in the subject, wherein the gene is operably linked to genetic regulatory elements such that the gene is expressed, and the expressed interferon protein is processed and secreted from the liver cells in an amount sufficient to treat the hepatitis infection.

2. The method of claim 1 wherein the gene encodes human interferon-α.

3. The method of claim 1 wherein the gene encodes human IFN-α2b.

4. The method of claim 1 wherein the gene is operably linked to the thyroxin binding globulin promoter in an expression vector.

5. The method of claim 1 wherein the cationic binding agent is a polycation.

6. The method of claim 5 wherein the cationic binding agent is polylysine.

7. The method of claim 1 wherein the ligand comprises a terminal carbohydrate residue.

8. The method of claim 1 wherein the ligand is an asialoglycoprotein.

9. The method of claim 1 wherein the ligand is selected from the group consisting of galactose, mannose and lactose.

10. The method of claim 1 wherein the molecular complex is administered intravenously.

11. The method of claim 1 wherein the hepatitus infection is Hepatitus-B virus or Hepatitus-C virus infection.

12. A method for treating hepatitis infection in a patient comprising administering to the patient a molecular complex comprising a gene encoding human interferon-α releasably linked to a conjugate of a polycation and a ligand which binds to the asialoglycoprotein receptor present on the surface of liver cells in the patient, the gene being linked to genetic regulatory elements such that the gene is expressed, and the expressed interferon protein is processed and secreted from the liver cells in an amount sufficient to treat the hepatitis infection when administered to the patient.

13. The method of claim 12 wherein the gene encodes human IFN-α2b.

14. The method of claim 12 wherein the hepatitus infection is Hepatitus-B virus or Hepatitis-C virus infection.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 166 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO: 1:

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
                20                  25                  30

Arg His Asp Phe Gly Phe Pro Gln Glu Glu Phe Xaa Gly Asn Gln Phe
            35                  40                  45

Gln Lys Ala Glu Thr Ile Pro Val Leu His Glu Met Ile Gln Gln Ile
        50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165
```

(2) INFORMATION FOR SEQ ID NO: 2:

(i) SEQUENCE CHARACTERISTICS:
      (A) LENGTH: 166 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO: 2:

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
                20                  25                  30

Arg His Asp Phe Gly Phe Pro Gln Glu Glu Phe Asp Gly Asn Gln Phe
            35                  40                  45

Gln Lys Ala Pro Ala Ile Ser Val Leu His Glu Leu Ile Gln Gln Ile
50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
                100                 105                 110

Asn Ala Asp Ser Ile Leu Ala Val Lys Lys Tyr Phe Arg Arg Ile Thr
                115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Leu Ser Thr Asn Leu Gln Glu
145                 150                 155                 160

Arg Leu Arg Arg Lys Glu
                165

(2) INFORMATION FOR SEQ ID NO: 3:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 3:

Arg Gln Lys Phe Ser Ser
1               5

(2) INFORMATION FOR SEQ ID NO: 4:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 4:

Arg Gln Thr Phe Ser Ser
1               5

(2) INFORMATION FOR SEQ ID NO: 5:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 5:

Arg Arg Lys Phe Ser Ser
1               5

(2) INFORMATION FOR SEQ ID NO: 6:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 6:

Lys Gln Lys Phe Ser Ser
1               5

(2) INFORMATION FOR SEQ ID NO: 7:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 7:

Lys Arg Lys Phe Ser Ser
1               5

(2) INFORMATION FOR SEQ ID NO: 8:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 8:

Arg Arg Thr Phe Ser Ser
1               5

(2) INFORMATION FOR SEQ ID NO: 9:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 9:

Lys Arg Thr Phe Ser Ser
1               5

```
(2) INFORMATION FOR SEQ ID NO: 10:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 10:

Arg His Lys Phe Ser Ser
1               5

(2) INFORMATION FOR SEQ ID NO: 11:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 11:

Arg Leu Lys Phe Ser Ser
1               5

(2) INFORMATION FOR SEQ ID NO: 12:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 12:

Arg Lys Thr Phe Ser Ser
1               5

(2) INFORMATION FOR SEQ ID NO: 13:

(i) SEQUENCE CHARACTERISTICS:
        (A) LENGTH: 166 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 13:

Cys Asp Leu Pro Gln Thr His Ser Leu Gly Ser Arg Thr Leu Met
1               5                   10                  15

Leu Leu Ala Gln Met Arg Arg Ile Ser Leu Phe Ser Cys Leu Lys Asp
                20                  25                  30

Arg His Asp Phe Gly Phe Pro Gln Glu Glu Phe Xaa Gly Asn Gln Phe
            35                  40                  45

Gln Lys Ala Glu Thr Ile Pro Val Leu His Glu Met Ile Gln Gln Ile
    50                  55                  60

Phe Asn Leu Phe Ser Thr Lys Asp Ser Ser Ala Ala Trp Asp Glu Thr
65                  70                  75                  80
```

-continued

```
Leu Leu Asp Lys Phe Tyr Thr Glu Leu Tyr Gln Gln Leu Asn Asp Leu
            85              90                  95

Glu Ala Cys Val Ile Gln Gly Val Gly Val Thr Glu Thr Pro Leu Met
            100             105             110

Lys Glu Asp Ser Ile Leu Ala Val Lys Lys Tyr Phe Arg Arg Ile Thr
        115             120             125

Leu Tyr Leu Lys Glu Lys Lys Tyr Ser Pro Cys Ala Trp Glu Val Val
    130             135             140

Arg Ala Glu Ile Met Arg Ser Phe Ser Leu Ser Thr Asn Leu Gln Glu
145             150             155                 160

Ser Leu Arg Ser Lys Glu
                165
```